United States Patent
Langemann et al.

(10) Patent No.: US 6,352,959 B1
(45) Date of Patent: Mar. 5, 2002

(54) THIOCHROMANOYLPYRAZOLONE DERIVATIVES

(75) Inventors: Klaus Langemann, Worms; Ernst Baumann, Dudenhofen; Wolfgang von Deyn, Neustadt; Steffen Kudis, Mannheim; Guido Mayer; Ulf Misslitz, both of Neustadt; Ulf Neidlein, Mannheim; Matthias Witschel, Ludwigshafen; Norbert Götz, Worms; Martina Otten, Ludwigshafen; Karl-Otto Westphalen, Speyer; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/857,053

(22) PCT Filed: Dec. 15, 1999

(86) PCT No.: PCT/EP99/09396

§ 371 Date: May 31, 2001

§ 102(e) Date: May 31, 2001

(87) PCT Pub. No.: WO00/34270

PCT Pub. Date: Jun. 15, 2000

(30) Foreign Application Priority Data

Dec. 4, 1998  (DE) .......................................... 198 56 048
Dec. 15, 1998 (DE) .......................................... 198 57 666

(51) Int. Cl.⁷ ........................ A01N 43/84; C07D 409/02
(52) U.S. Cl. ...................... 504/282; 544/140; 548/119; 548/159; 548/255; 548/266.4; 548/364.4
(58) Field of Search .............................. 548/364.4, 159; 504/282

(56) References Cited

U.S. PATENT DOCUMENTS 5,925,767 A   7/1999   Otten

FOREIGN PATENT DOCUMENTS

| CA | 2227946 | 3/1997 |
|---|---|---|
| DE | 195 32 312 | 3/1997 |
| WO | 97/30993 | 8/1997 |
| WO | 99/5991 | 11/1999 |

*Primary Examiner*—Robert W. Ramsuer
(74) *Attorney, Agent, or Firm*—Keil & Weinkauf

(57) ABSTRACT

Thiochromanoylpyrazolone derivatives of the formula I

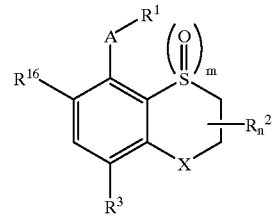

where:

A is an unsubstituted or substituted, saturated or unsaturated alkyl chain;

$R^1$ is cyano, thiocyanato, nitro, $OR^4$, $SR^5$, $SOR^6$, $SO_2R^6$, $ONR^6NR^7$, $ON=CR^6R^8$, $NR^9R^{10}$, $P(O)R^{11}R^{12}$, $P(S)R^{11}R^{12}$, $COR$, $CO_2R^6$, unsubstituted or substituted phenyl or heterocyclyl;

$R^2$ is alkyl, haloalkyl, alkoxy or haloalkoxy;

$R^3$ is hydrogen, alkyl or halogen;

X is oxygen, sulfur, S=O, $S(=O)_2$, $CR^{13}R^{14}$, C=O or $C=NR^{15}$;

m is 0, 1 or 2;

n is 0, 1, 2, 3 or 4;

$R^{16}$ is substituted pyrazol-4-yl-carbonyl or substituted (4,5-dihydro-5-oxo-pyrazol-4-yl)methylidene;

and their agriculturally useful salts;

Processes for preparing the thiochromanoylpyrazolone derivatives, compositions comprising them, and the use of these derivatives or of the compositions comprising them for controlling undesirable plants are described.

10 Claims, No Drawings

THIOCHROMANOYLPYRAZOLONE DERIVATIVES

This application is a 371 of PCT/EP99/09346 filed Dec. 15, 1999.

The present invention relates to novel thiochromanoylpyrazolone derivatives of the formula I

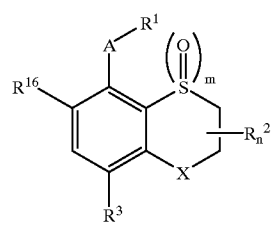

where:

A is $C_1$–$C_6$-alkanediyl, $C_2$–$C_6$-alkenediyl, $C_4$–$C_6$-alkadienediyl or $C_2$–$C_6$-alkinediyl, where the above-mentioned radicals may carry one or two substituents from the following group: cyano, $C_1$–$C_4$-alkoxy, $C_1$–$C_4$-alkylthio, $C_1$–$C_4$-alkylcarbonyl or $C_1$–$C_4$-alkoxycarbonyl;

$R^1$ is cyano, thiocyanato, nitro, $OR^4$, $SR^5$, $SOR^6$, $SO_2R^6$, $ONR^6R^7$, $ON{=}CR^6R^8$, $NR^9R^{10}$, $P(O)R^{11}R^{12}$, $P(S)R^{11}R^{12}$, $COR^6$, $CO_2R^6$, phenyl, heterocyclyl or N-bonded heterocyclyl, where the three last-mentioned radicals for their part may be partially or fully halogenated and/or may carry one to three substituents from the following group: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^2$ is $C_1$–$C_6$-alkyl, $C_1$–$C_6$-haloalkyl, $C_1$–$C_6$-alkoxy or $C_1$–$C_6$-haloalkoxy;

$R^3$ is hydrogen, halogen or $C_1$–$C_6$-alkyl;

X is oxygen, sulfur, S=O, S(=O)$_2$, $CR^{13}R^{14}$, C=O or C=NR$^{15}$;

m is 0, 1 or 2;

n is 0, 1, 2, 3 or 4;

$R^4$, $R^5$ are one of the radicals mentioned under $R^6$;
are hydrogen, $C_1$–$C_4$-alkylcarbonyl, $C_1$–$C_4$-haloalkylcarbonyl, $C_1$–$C_4$-alkoxycarbonyl, $C_1$–$C_4$-haloalkoxycarbonyl, $C_1$–$C_4$-alkylsulfonyl, $C_1$–$C_4$-haloalkylsulfonyl, $P(O)R^{11}R^{12}$ or $P(S)R^{11}R^{12}$;
are phenylcarbonyl, phenoxycarbonyl, phenyl-$C_1$–$C_4$-alkylcarbonyl, phenylsulfonyl, phenoxysulfonyl, heterocyclylcarbonyl, heterocyclyloxycarbonyl, heterocyclyl-$C_1$–$C_4$-alkylcarbonyl, heterocyclylsulfonyl or heterocyclyloxysulfonyl, where the phenyl and the heterocyclyl radical of the ten last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^6$ is $C_1$–$C_6$-alkyl, $C_3$–$C_6$-alkenyl, $C_3$–$C_6$-alkynyl or $C_3$–$C_6$-cycloalkyl, where the four abovementioned radicals may be partially or fully halogenated and/or may carry one to three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl, $C_1$–$C_4$-alkylcarbonyl, $C_1$–$C_4$-alkoxycarbonyl and $C_1$–$C_4$-haloalkoxycarbonyl;
is phenyl, phenyl-$C_1$–$C_4$-alkyl, heterocyclyl or heterocyclyl-$C_1$–$C_4$-alkyl, where the phenyl and the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^7$ is hydrogen or $C_1$–$C_6$-alkyl;

$R^8$ is hydrogen, $C_1$–$C_6$-alkyl, $C_1$–$C_6$-alkoxycarbonyl, cyano or $C_1$–$C_6$-alkoxy;

$R^9$ is one of the radicals mentioned under $R^4$; is $C_1$–$C_6$-alkoxy, $C_3$–$C_6$-alkenyloxy, $C_3$–$C_6$-alkynyloxy, aminocarbonyl, N—$C_1$–$C_6$-alkylaminocarbonyl or N,N-di-($C_1$–$C_6$-alkyl)aminocarbonyl;

$R^{10}$ is hydrogen, $C_1$–$C_6$-alkyl, $C_3$–$C_6$-alkenyl or $C_3$–$C_6$-alkynyl;

$R^{11}$, $R^{12}$ are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{13}$, $R^{14}$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, N—$C_1$–$C_6$-alkylamino, N—$C_1$–$C_6$-haloalkylamino, N,N-(di-$C_1$–$C_6$-alkyl)amino, N—$C_1$–$C_6$-alkoxyamino, N—($C_1$–$C_6$-alkoxy)-N—($C_1$–$C_6$-alkyl)amino, 1-tetrahydropyrrolyl, 1-piperidinyl, 4-morpholinyl or 1-hexahydropyrazinyl;

or $R^{13}$, $R^{14}$ together form a methylidene group which may be substituted by one or two substituents from the following group: halogen, cyano, $C_1$–$C_6$-alkyl, $C_1$–$C_6$-haloalkyl, $C_1$–$C_6$-alkoxy or $C_1$–$C_6$-haloalkoxy;

$R^{15}$ is $C_1$–$C_6$-alkyl, $C_1$–$C_6$-haloalkyl, $C_1$–$C_6$-alkoxy or $C_1$–$C_6$-haloalkoxy;

$R^{16}$ is a radical IIa or IIb,

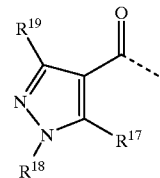

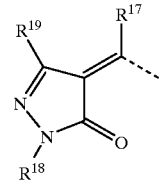

where:

$R^{17}$ is hydroxyl, mercapto, halogen, $OR^{20}$, $SR^{20}$, $SOR^{21}$, $SO_2R^{21}$, $OSO_2R^{21}$, $P(O)R^{22}R^{23}$, $OP(O)R^{22}R^{23}$, $P(S)$ $R^{22}R^{23}$, $OP(S)R^{22}R^{23}$, $NR^{24}R^{25}$, $ONR^{21}R^{21}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$ is hydrogen, $C_1$–$C_6$-alkyl, $C_1$–$C_6$-haloalkyl, hydroxyl, $C_1$–$C_6$-alkoxy or $C_1$–$C_6$-haloalkoxy;

$R^{19}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio;

$R^{20}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di-($C_1$–$C_6$-alkyl)aminocarbonyl, N—($C_3$–$C_6$-alkenyl)-N—($C_1$–$C_6$-alkyl)aminocarbonyl, N—($C_3$–$C_6$-alkynyl)-N—($C_1$–$C_6$-alkyl)aminocarbonyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl, N—($C_3$–$C_6$-alkynyl)-N—($C_1$–$C_6$-alkoxy)aminocarbonyl, di-($C_1$–$C_6$-alkyl)aminothiocarbonyl or $C_1$–$C_6$-alkoxyimino-$C_1$–$C_6$-alkyl, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenyloxythiocarbonyl, phenylaminocarbonyl, N—($C_1$–$C_6$-alkyl)-N-(phenyl)aminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylaminocarbonyl, N—($C_1$–$C_6$-alkyl)-N-(heterocyclyl)aminocarbonyl or heterocyclyl-$C_2$–$C_6$-alkenylcarbonyl, where the phenyl and the heterocyclyl radical of the 18 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{21}$ is $C_1$–$C_6$-alkyl, $C_3$–$C_6$-alkenyl, $C_3$–$C_6$-alkynyl or $C_3$–$C_6$-cycloalkyl, where the four abovementioned radicals may be partially or fully halogenated and/or may carry one to three of the following groups:

cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_6$-alkyl, heterocyclyl or heterocyclyl-$C_1$–$C_6$-alkyl, where the phenyl and the heterocyclyl radical of the last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{22}$, $R^{23}$ is hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{24}$ is hydrogen, $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three of the following radicals: cyano, $C_1$–$C_4$-alkoxycarbonyl, $C_1$–$C_4$-alkylaminocarbonyl, di-($C_1$–$C_4$-alkyl)aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{25}$ is hydrogen, $C_1$–$C_6$-alkyl, $C_3$–$C_6$-alkenyl or $C_3$–$C_6$-alkynyl;

and its agriculturally useful salts.

Moreover, the invention relates to processes for preparing compounds of the formula I, to compositions comprising them and to the use of these derivatives or of compositions comprising them for controlling harmful plants.

WO 97/30993 and WO 97/09327 disclose dioxothiochroman derivatives which are linked to a substituted (5-hydroxypyrazol-4-yl)carbonyl radical. However, the herbicidal properties of the prior art compounds and their compatibility with crop plants are not entirely satisfactory. It is an object of the present invention to provide novel, biological, in particular herbicidally active, compounds having improved properties.

This object is achieved by the thiochromanoylpyrazolone derivatives of the formula I and their herbicidal action.

Furthermore, we have found herbicidal compositions which comprise the compounds I and have very good herbicidal activity. Moreover, we have found processes for preparing these compositions and methods for controlling undesirable vegetation using the compounds I.

Depending on the substitution pattern, the compounds of the formula I can contain one or more chiral centers, in which case they are present as enantiomers or mixtures of diastereomers. This invention provides both the pure enantiomers or diastereomers and mixtures thereof.

The compounds of the formula I can also be present in the form of their agriculturally useful salts, where the type of salt is usually immaterial. In general, suitable salts are the salts of those cations or the acid addition salts of those acids whose cations and anions, respectively, do not negatively affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where here, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$–$C_4$-alkyl)sulfonium, and sulfoxonium ions, preferably tri ($C_1$–$C_4$-alkyl)sulfoxonium.

Anions of useful acid additions salts are primarily chloride, bromide, fluorine, hydrogen sulfate, sulfate, dihydrogen phosphate, hydrogen phosphate, nitrate, hydrogen carbonate, carbonate, hexafluorosilicate, hexafluorophosphate, benzoate, and also the anions of $C_1$–$C_4$-alkanoic acids, preferably formate, acetate, propionate and butyrate.

In the case that $R^{17}$=hydroxyl or mercapto {Y=O,S}, IIa also represents, in lieu, the tautomeric forms IIa' and IIa''

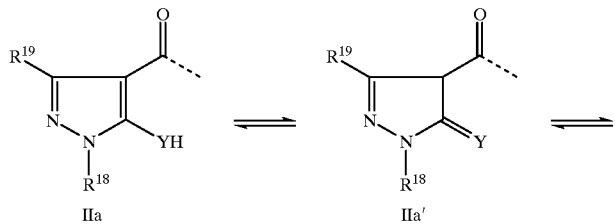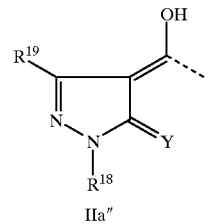

and IIb also represents, in lieu, the tautomeric forms IIb' and IIb''.

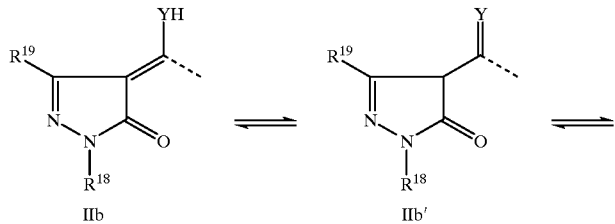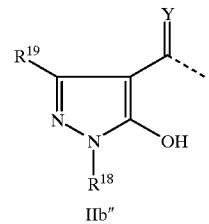

The organic molecular moieties mentioned for the substituents $R^1$–$R^{25}$ or as radicals on phenyl and heterocyclyl radicals are collective terms for individual enumerations of the individual group members. All hydrocarbon chains, i.e. all alkyl, haloalkyl, alkoxy, haloalkoxy, alkylthio, haloalkylthio, alkylsulfinyl, haloalkylsulfinyl, alkylsulfonyl, haloalkylsulfonyl, N-alkylamino, N,N-dialkylamino, N-haloalkylamino, N-alkoxyamino, N-alkoxy-N-alkylamino, N-alkylcarbonylamino, alkylcarbonyl, haloalkylcarbonyl, alkoxycarbonyl, haloalkoxycarbonyl, alkylthiocarbonyl, alkylcarbonyloxy, alkylaminocarbonyl, dialkylaminocarbonyl, dialkylaminothiocarbonyl, alkoxyalkyl, alkoxyiminoalkyl, phenylalkylcarbonyl, heterocyclylalkylcarbonyl, phenylalkenylcarbonyl, heterocyclylalkenylcarbonyl, N-alkoxy-N-alkylaminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl, alkenyloxy, alkynyloxy, alkanediyl, alkenediyl, alkadienediyl or alkynediyl moities can be straight-chain or branched. Unless indicated otherwise, halogenated substituents preferably carry one to five identical or different halogen atoms. The term halogen represents in each case fluorine, chlorine, bromine or iodine.

Examples of other meanings are:

$C_1$–$C_4$-alkyl, and the alkyl moieties of phenyl-$C_1$–$C_4$-alkyl, heterocyclyl-$C_1$–$C_4$-alkyl, phenyl-$C_1$–$C_4$-alkylcarbonyl or heterocyclyl-$C_1$–$C_4$-alkylcarbonyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkoxyimino-$C_1$–$C_6$-alkyl, N—($C_1$–$C_6$-alkoxy) -N—($C_1$–$C_6$-alkyl) amino, N—($C_1$–$C_6$-alkoxy) -N—($C_1$–$C_6$-alkyl)aminocarbonyl, N—($C_3$–$C_6$-alkenyl)-N—($C_1$–$C_6$-alkyl)aminocarbonyl, ($C_3$–$C_6$-alkynyl)-N—($C_1$–$C_6$-alkyl)aminocarbonyl, N—($C_1$–$C_6$-alkyl)-N-phenylaminocarbonyl, N—($C_1$–$C_6$-alkyl)-N-heterocyclylaminocarbonyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 1-fluoroethyl, 1-bromoethyl, 1-chloroethyl, 1-iodoethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of N—$C_1$–$C_6$-haloalkylamino: ($C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of N—$C_1$–$C_6$-alkoxyamino, N—$C_1$–$C_6$-alkoxy-N—$C_1$–$C_6$-alkylamino, $C_1$–$C_6$-alkoxyimino-$C_1$–$C_6$-alkyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)-aminocarbonyl and N—($C_3$–$C_6$-alkynyl)-N—($C_1$–$C_6$-alkoxy)-aminocarbonyl: $C_1$–$C_4$-alkoxy, as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2--dimethylbutoxy, 1,3-dimethylbutoxy, 2,2-dimethylbutoxy, 2,3--dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical, as mentioned above, which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy, as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio or 1,1-dimethylethylthio;

$C_1$–$C_6$-alkylthio: and the alkylthio moieties of $C_1$–$C_6$-alkylthiocarbonyl: $C_1$–$C_4$-alkylthio, as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_4$-haloalkylthio: a $C_1$–$C_4$-alkylthio radical, as mentioned above, which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_6$-haloalkylthio: $C_1$–$C_4$-haloalkylthio, as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_4$-alkylsulfinyl ($C_1$–$C_4$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl or 1,1-dimethylethylsulfinyl;

$C_1$–$C_6$-alkylsulfinyl: $C_1$–$C_4$-alkylsulfinyl radical, as mentioned above, and also pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_4$-haloalkylsulfinyl: $C_1$–$C_4$-alkylsulfinyl, as mentioned above, which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl;

$C_1$–$C_6$-haloalkylsulfinyl: $C_1$–$C_4$-haloalkylsulfinyl, as mentioned above, and also 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_4$-alkylsulfonyl ($C_1$–$C_4$-alkyl-S(=O)$_2$—), for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl;

$C_1$–$C_6$-alkylsulfonyl: $C_1$–$C_4$-alkylsulfonyl, as mentioned above, and also pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_4$-haloalkylsulfonyl: a $C_1$–$C_4$-alkylsulfonyl radical, as mentioned above, which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl;

$C_1$–$C_6$-haloalkylsulfonyl: $C_1$–$C_4$-haloalkylsulfonyl, as mentioned above, and also 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino, and the alkylamino radicals of N—($C_1$–$C_6$-alkoxy)-N—($C_1$–$C_6$-alkyl)amino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di-($C_1$–$C_4$-alkyl)amino: for example N,N-dimethylamino, N,N-diethylamino, N,N-dipropylamino, N,N-di-(1-methylethyl) amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di-($C_1$–$C_6$-alkyl)amino: di-($C_1$–$C_4$-alkyl)amino, as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonylamino: $C_1$–$C_4$-alkylcarbonyl, as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_4$-haloalkylcarbonyl: a $C_1$–$C_4$-alkylcarbonyl radical as, mentioned above, which is partially or fully substituted by fluorine, chlorine, bromine and/or iodine, i.e., for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl;

$C_1$–$C_6$-haloalkylcarbonyl: a $C_1$–$C_4$-haloalkylcarbonyl radical as mentioned above, and also 5-fluoropentylcarbonyl, 5-chloropentylcarbonyl, 5-bromopentylcarbonyl, perfluoropentylcarbonyl, 6-fluorohexylcarbonyl, 6-chlorohexylcarbonyl, 6-bromohexylcarbonyl or perfluorohexylcarbonyl;

$C_1$–$C_4$-alkoxycarbonyl: for example, methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$–$C_6$-alkoxycarbonyl: $C_1$–$C_4$-alkoxycarbonyl, as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2--ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_4$-haloalkoxycarbonyl: a $C_1$–$C_4$-alkoxycarbonyl radical, as mentioned above, which is partially or fully substituted by fluorine, chlorine, bromine and/or iodine, i.e., for example, fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl or 4-iodobutoxycarbonyl;

$C_1$–$C_6$-haloalkoxycarbonyl: a $C_1$–$C_4$-haloalkoxycarbonyl radical as mentioned above, and also 5-fluoropentoxycarbonyl, 5-chloropentoxycarbonyl, 5-bromopentoxycarbonyl, 6-fluorohexoxycarbonyl, 6-chlorohexoxycarbonyl or 6-bromohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino) carbonyl, as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di-($C_1$–$C_4$-alkyl)aminocarbonyl: for example N,N-dimethylaminocarbonyl, N,N-diethylaminocarbonyl, N,N-di-(1-methylethyl)aminocarbonyl, N,N-dipropylaminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di-($C_1$–$C_6$-alkyl)aminocarbonyl: di-($C_1$–$C_4$-alkyl)aminocarbonyl, as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di-($C_1$–$C_6$-alkyl)aminothiocarbonyl: for example N,N-dimethylaminothiocarbonyl, N,N-diethylaminothiocarbonyl, N,N-di-(1-methylethyl)aminothiocarbonyl, N,N-dipropylaminothiocarbonyl, N,N-dibutylaminothiocarbonyl, N,N-di-(1-methylpropyl)aminothiocarbonyl, N,N-di-(2-methylpropyl)aminothiocarbonyl, N,N-di-(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-methylpropyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_4$-alkoxy-$C_1$–$C_4$-alkyl: $C_1$–$C_4$-alkyl, which is substituted by $C_1$–$C_4$-alkoxy, as mentioned above, i.e. for example, for methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)-butyl, 3-(1-methylpropoxy)butyl, 3-(2-methylpropoxy)butyl, 3-(1,1-dimethylethoxy)butyl, 4-(methoxy)butyl, 4-(ethoxy)-butyl, 4-(propoxy)butyl, 4-(1-methylethoxy)butyl, 4-(butoxy)-butyl, 4-(1-methylpropoxy)butyl, 4-(2-methylpropoxy)butyl or 4-(1,1-dimethylethoxy)butyl;

$C_1$–$C_4$-alkoxy-$C_1$–$C_4$-alkoxy, and the alkoxyalkoxy moieties of $C_1$–$C_4$-alkoxy-$C_1$–$C_4$-alkoxycarbonyl: $C_1$–$C_4$-alkoxy which is substituted by $C_1$–$C_4$-alkoxy, as mentioned above, i.e., for example, for methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl-, $C_3$–$C_6$-alkenylaminocarbonyl, N—($C_3$–$C_6$-alkenyl)-N—($C_1$–$C_6$-alkyl)aminocarbonyl, N—($C_3$–$C_6$-alkenyl)-N—($C_1$–$C_6$-alkoxy)aminocarbonyl: for example prop-2-en-1-yl, but-1-en-4-yl, 1-methyl-prop-2-en-1-yl, 2-methyl-prop-2-en-1-yl, 2-butene-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl, as mentioned above, and also ethenyl;

$C_3$–$C_6$-haloalkenyl: a $C_3$–$C_6$-alkenyl radical, as mentioned above, which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N—($C_3$–$C_6$-alkynyl)-N—($C_1$–$C_6$-alkyl)aminocarbonyl, N—($C_3$–$C_6$-alkynyl)-N—($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: ($_3$–$C_6$-alkynyl, as mentioned above, and also ethynyl;

$C_3$–$C_6$-haloalkynyl: a $C_3$–$C_6$-alkynyl radical, as mentioned above, which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$–$C_6$-alkanediyl: methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane--1,3-diyl, butane-1,4-diyl, 2-methylpropane-1,3-diyl, 2-methylpropane-1,2-diyl, 2-methylpropane-1,1-diyl, 1-methylpropane-1,2-diyl, 1-methylpropane-2,2-diyl, 1-methylpropane-1,1-diyl, pentane-1,1-diyl, pentane-1,2-diyl, pentane-1,3-diyl, pentane-1,5-diyl, pentane-2,3-diyl, pentane-2,2-diyl, 1-methylbutane-1,1-diyl, 1-methylbutane-1,2-diyl, 1-methylbutane-1,3-diyl, 1-methylbutane-1,4-diyl, 2-methylbutane-1,1-diyl, 2-methylbutane-1,2-diyl, 2-methylbutane-1,3-diyl, 2-methylbutane-1,4-diyl, 2,2-dimethylpropane-1,1-diyl, 2,2-dimethylpropane-1,3-diyl, 1,1-dimethylpropane-1,3-diyl, 1,1-dimethylpropane-1,2-diyl, 2,3-dimethylpropane-1,3-diyl, 2,3-dimethylpropane-1,2-diyl, 1,3-dimethylpropane-1,3-diyl, hexane-1,1-diyl, hexane-1,2-diyl, hexane-1,3-diyl, hexane-1,4-diyl, hexane-1,5-diyl, hexane-1,6-diyl, hexane-2,5-diyl, 2-methylpentan-1,1-diyl, 1-methylpentane-1,2-diyl, 1-methylpentane-1,3-diyl, 1-methylpentane-1,4-diyl, 1-methylpentane-1,5-diyl, 2-methylpentane-1,1-diyl, 2-methylpentane-1,2-diyl, 2-methylpentane-1,3-diyl, 2-methylpentane-1,4-diyl, 2-methylpentane-1,5-diyl, 3-methylpentane-1,1-diyl, 3-methylpentane-1,2-diyl, 3-methylpentane-1,3-diyl, 3-methylpentane-1,4-diyl, 3-methylpentane-1,5-diyl, 1,1-dimethylbutane-1,2-diyl, 1,1-dimethylbutane-1,3-diyl, 1,1-dimethylbutane-1,4-diyl, 1,2-dimethylbutane-1,1-diyl, 1,2-dimethylbutane-1,2-diyl, 1,2-dimethylbutane-1,3-diyl, 1,2-dimethylbutane-1,4-diyl, 1,3-dimethylbutane-1,1-diyl, 1,3-dimethylbutane-1,2-diyl, 1,3-dimethylbutane-1,3-diyl, 1,3-dimethylbutane-1,4-diyl, 1-ethylbutane-1,1-diyl, 1-ethylbutane-1,2-diyl, 1-ethylbutane-1,3-diyl, 1-ethylbutane-1,4-diyl, 2-ethylbutane-1,1-diyl, 2-ethylbutane-1,2-diyl, 2-ethylbutane-1,3-diyl, 2-ethylbutane-1,4-diyl, 2-ethylbutane-2,3-diyl, 2,2-dimethylbutane-1,1-diyl, 2,2-dimethylbutane-1,3-diyl, 2,2-dimethylbutane-1,4-diyl, 1-isopropylpropane-1,1-diyl, 1-isopropylpropane-1,2-diyl, 1-isopropylpropane-1,3-diyl, 2-isopropylpropane-1,1-diyl, 2-isopropylpropane-1,2-diyl, 2-isopropylpropane-1,3-diyl, 1,2,3-trimethylpropane-1,1-diyl, 1,2,3-trimethylpropane-1,2-diyl or 1,2,3-trimethylpropane-1,3-diyl;

$C_2$–$C_6$-alkenediyl: ethene-1,1-diyl, ethene-1,2-diyl, 1-propene-1,1-diyl, 1-propene-1,2-diyl, 1-propene-1,3-diyl, 2-propene-1,1-diyl, 2-propene-1,2-diyl, 2-propene-1,3-diyl, 1-butene-1,1-diyl, 1-butene-1,2-diyl, 1-butene-1,3-diyl, 1-butene-1,4-diyl, 2-butene-1,1-diyl, 2-butene-1,2-diyl, 2-butene-1,3-diyl, 2-butene-1,4-diyl, 3-butene-1,1-diyl, 3-butene-1,2-diyl, 3-butene-1,3-diyl, 3-butene-1,4-diyl, 1-methyl-1-propene-1,2-diyl, 1-methyl-1-propene-1,3-diyl, 1-methyl-2-propene-1,1-diyl, 1-methyl-2-propene-1,2-diyl, 1-methyl-2-propene-1,3-diyl, 2-methyl-1,1-propene-1,1-diyl, 2-methyl-1-propene-1,3-diyl, 3-butene-1,1-diyl, 3-butene-1,2-diyl, 3-butene-1,3-diyl, 3-butene-1,4-diyl, 1-penten-1,1-diyl, 1-penten-1,2-diyl, 1-penten-1,3-diyl, 1-penten-1,4-diyl, 1-penten-1,5-diyl, 1-hexene-1,1-diyl, 1-hexene-1,2-diyl, 1-hexene-1,3-diyl, 1-hexene-1,4-diyl, 1-hexene-1,5-diyl or 1-hexene-1,6-diyl;

$C_2$–$C_6$-alkdienediyl: 1,3-butadiene-1,1-diyl, 1,3-butadiene-1,2-diyl, 1,3-butadiene-1,3-diyl, 1,3-butadiene-1,4-diyl, 1,3-pentadiene-1,1-diyl, 1,3-pentadiene-1,2-diyl, 1,3-pentadiene-1,3-diyl, 1,3-pentadiene-1,4-diyl, 1,3-pentadiene-1,5-diyl, 2,4-pentadiene-1,1-diyl, 2,4-pentadiene-1,2-diyl, 2,4-pentadiene-1,3-diyl, 2,4-pentadiene-1,4-diyl, 2,4-pentadiene-1,5-diyl, 1-methyl-1,3-butadiene-1,4-diyl, 1,3-hexadiene-1,1-diyl, 1,3-hexadiene-1,2-diyl, 1,3-hexadiene-1,3-diyl, 1,3-hexadiene-1,4-diyl, 1,3-hexadiene-1,5-diyl, 1,3-hexadiene-1,6-diyl, 1-methyl-1,3-pentadiene-1,2-diyl, 1-methyl-1,3-pentadiene-1,3-diyl, 1-methyl-1,3-pentadiene-1,4-diyl or 1-methyl-1,3-pentadiene-1,5-diyl;

$C_2$–$C_6$-alkynediyl: ethyne-1,2-diyl, 1-propyne-1,3-diyl, 2-propyne-1,1-diyl, 2-propyne-1,3-diyl, 1-butyne-1,3-diyl, 1-butyne-1,4-diyl, 2-butyne-1,1-diyl, 2-butyne-1,4-diyl, 1-methyl-2-propyne-1,1-diyl, 1-methyl-2-propyne-1,3-diyl, 1-pentyne-1,3-diyl, 1-pentyne-1,4-diyl, 1-pentyne-1,5-diyl, 2-pentyne-1,1-diyl, 2-pentyne-1,4-diyl, 2-pentyne-1,5-diyl, 3-pentyne-1,1-diyl, 3-pentyne-1,2-diyl, 3-pentyne-1,5-diyl, 4-pentyne-1,1-diyl, 4-pentyne-1,2-diyl, 4-pentyne-1,3-diyl, 4-pentyne-1,5-diyl, 1-hexyne-1,3-diyl, 1-hexyne-1,4-diyl, 1-hexyne-1,5-diyl, 1-hexyne-1,6-diyl, 2-hexyne-1,1-diyl, 2-hexyne-1,4-diyl, 2-hexyne-1,5-diyl, 2-hexyne-1,6-diyl, 3-hexyne-1,1-diyl, 3-hexyne-1,2-diyl, 3-hexyne-1,5-diyl, 3-hexyne-1,6-diyl, 4-hexyne-1,1-diyl, 4-hexyne-1,2-diyl, 4-hexyne-1,3-diyl, 4-hexyne-1,6-diyl, 5-hexyne-1,1-diyl, 5-hexyne-1,2-diyl, 5-hexyne-1,3-diyl, 5-hexyne-1,4-diyl or 5-hexyne-1,6-diyl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and the heterocyclyl moieties of heterocyclyloxy, heterocyclylcarbonyl, heterocyclyl-$C_1$–$C_4$-alkyl, heterocyclyl-$C_1$–$C_6$-alkyl, heterocyclylsulfonyl or heterocyclyloxysulfonyl, heterocyclyloxycarbonyl, heterocyclyloxythiocarbonyl, heterocyclyl-$C_2$–$C_6$-alkenylcarbonyl, heterocyclylcarbonyl-$C_1$–$C_6$-alkyl, N—($C_1$–$C_6$-alkyl)-N-(heterocyclyl)aminocarbonyl, heterocyclylaminocarbonyl: a saturated, partially saturated or unsaturated 5- or 6-membered, C-bonded, heterocyclic ring which contains one to four identical or different heteroatoms selected from the following group: oxygen, sulfur or nitrogen, i.e., for example, 5-membered rings with one heteroatom such as:
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl or pyrrol-3-yl;

5-membered rings with two heteroatoms, such as tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl or thiazol-5-yl;

5-membered rings with three heteroatoms, such as 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl or 1,2,4-triazol-3-yl;

5-membered rings with four heteroatoms, such as tetrazol-5-yl, 6-membered rings with one heteroatom, such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl or pyridin-4-yl;

6-membered rings with two heteroatoms, such as 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3- yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl, 3,4-dihydropyrimidin-6-yl, pyridazin-3-yl, pyridazin-4-yl, pyrimidin-2-yl, pyrimidin-4-yl, pyrimidin-5-yl or Pyrazin-2-yl;

6-membered rings with three heteroatoms, such as 1,3,5-triazin-2-yl, 1,2,4-triazin-3-yl, 1,2,4-triazin-5-yl, 1,2,4-triazin-6-yl or 6-membered rings with four heteroatoms, such as 1,2,4,5-tetrazin-3-yl;

where the sulfur of the abovementioned heterocycles may be oxidized to give S=O or S(=O)$_2$;

and where a bicyclic ring system may be formed with a fused-on phenyl ring or with a $C_3$–$C_6$-carbocycle or another 5- to 6-membered heterocycle.

N-bonded heterocyclyl: a saturated, partially saturated or unsaturated 5- or 6-membered N-bonded heterocyclic ring which contains at least one nitrogen and which may contain one to three identical or different heteroatoms selected from the following group: oxygen, sulfur or nitrogen, i.e., for example, N-bonded 5-membered rings with one heteroatoms, such as: tetrahydropyrrol-1-yl, 2,3-dihydro-1H-pyrrol-1-yl, 2,5-dihydro-1H-pyrrol-1-yl or pyrrol-1-yl;

N-bonded 5-membered rings with two heteroatoms, such as tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl or imidazol-1-yl;

N-bonded 5-membered rings with three heteroatoms, such as 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl or 1,2,4-triazol-1-yl;

N-bonded 5-membered rings with four heteroatoms, such as tetrazol-1-yl;

and also N-bonded 6-membered rings with one heteroatom, such as:
piperidin-1-yl, 1,2,3,4-tetrahydropyridin-1-yl, 1,2,5,6-tetrahydropyridin-1-yl, 1,4-dihydropyridin-1-yl or 1,2-dihydropyridin-1-yl;

N-bonded 6-membered rings with two heteroatoms, such as hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl, 2H-5,6-dihydro-1,2-oxazin-2-yl, 2H-5, 6-dihydro-1,2-thiazin-2-yl, 2H-3,6-dihydro-1,2-oxazin-2-yl, 2H-3, 6-dihydro-1,2-thiazin-2-yl, 2H-3,4-dihydro-1,2-thiazin-2-yl, 2,3,4, 5-tetrahydropyridazin-2-yl, 1,2,5, 6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

and also N-bonded cyclic imides such as:
phthalimide, tetrahydrophthalimide, succinimide, maleinimide or glutarimide; 5-oxo-triazolin-1-yl, 5-oxo-1,3,4-oxadiazolin-4-yl or 2,4-dioxo-(1H, 3H)-pyrimidin-3-yl;

where, with a fused-on phenyl ring or with a $C_3$–$C_6$-carbocycle or a further 5- to 6-membered heterocycle, a bicyclic ring system may be formed.

All phenyl rings and heterocyclyl radicals, and all phenyl components in phenoxy, phenylalkyl, phenylcarbonylalkyl, phenylcarbonyl, phenylalkenylcarbonyl, phenoxycarbonyl, phenyloxythiocarbonyl, phenylaminocarbonyl, N-alkyl-N-phenylaminocarbonyl, phenylsulfonyl or phenoxysulfonyl and heterocyclyl components in heterocyclyloxy, heterocyclylalkyl, heterocyclylcarbonylalkyl, heterocyclylcarbonyl, heterocyclyloxythiocarbonyl, heterocyclylalkenylcarbonyl, heterocyclyloxycarbonyl, heterocyclylaminocarbonyl, N-alkyl-N-heterocyclylaminocarbonyl, heterocyclylsulfonyl or heterocyclyloxysulfonyl are, unless stated otherwise, preferably unsubstituted, or they carry one to three halogen atoms and/or one nitro group, one cyano radical and/or one or two methyl, trifluoromethyl, methoxy or trifluoromethoxy substituents.

The compounds of the formula I according to the invention where $R^{16}$=IIa are referred to as compounds of the formula Ia, and compounds of the formula I where $R^{16}$=IIb are referred to as Ib.

With a view to the use of the compounds of the formula I according to the invention as herbicides, the variables preferably have the following meanings, in each case on their own or in combination:

A is $C_1$–$C_6$-alkanediyl or $C_2$–$C_6$-alkenediyl, where the abovementioned radicals may carry one or two substituents from the following group: cyano, $C_1$–$C_4$-alkoxy, $C_1$–$C_4$-alkylthio, $C_1$–$C_4$-alkylcarbonyl or $C_1$–$C_4$-alkoxycarbonyl; preferably $C_1$–$C_4$-alkanediyl, such as methane-1,1-diyl, ethane-1,1-diyl or ethane-1,2-diyl, or $C_2$–$C_4$-alkenediyl, such as ethene-1,1-diyl, ethene-1,2-diyl, 1-methyl-ethene-1,2-diyl or 1-propene-1,2-diyl;

particularly preferably methane-1,1-diyl or ethene-1,2-diyl;

$R^1$ is cyano, thiocyanato, nitro, $OR^4$, $SR^5$, $SOR^6$, $SO_2R^6$, $ONR^6R^7$, $ON=CR^6R^8$, $NR^9R^{10}$, $P(O)R^{11}R^{12}$, $P(S)R^{11}R^{12}$, $COR^6$, $CO_2R^6$ or N-bonded heterocyclyl, where the lastmentioned radical for its part may be partially or fully halogenated and/or may carry one to three substituents from the following group: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl; preferably cyano, thiocyanato, nitro, $OR^4$, $SR^5$, $SO_2R^6$, $ONR^6R^7$, $ON=CR^6R^7$, $NR^9R^{10}$, $P(O)R^{11}R^{12}$, $P(S)R^{11}R^{12}$, $COR^6$, $CO_2R^6$ or N-bonded heterocyclyl, such as pyrazol-1-yl, imidazol-1-yl, 1,2,4-triazol-1-yl, pyrrolidin-1-yl, tetrahydroisoxazol-2-yl or morpholin-4-yl; particularly preferably cyano, nitro, $OR^4$, $SO_2R^6$, $ONR^6R^7$, $P(O)R^{11}R^{12}$, $P(S)R^{11}R^{12}$, $COR^6$ or $CO_2R^6$;

$R^2$ is $C_1$–$C_4$-alkyl, such as methyl, ethyl, propyl or 1-methylethyl;

$R^3$ is hydrogen, halogen, such as fluorine, chlorine or bromine, or $C_1$–$C_4$-alkyl, such as methyl or ethyl; particularly preferably hydrogen, chlorine or methyl; very particularly preferably hydrogen;

X is $S(=O)_2$, $CR^{13}R^{14}$ or $C=O$; preferably $S(=O)_2$ or $CR^{13}R^{14}$;

m is 0, 1 or 2; preferably 2;

n is 0, 1, 2, 3 or 41; preferably 0,1 or 2; particularly preferably 0;

$R^4$, $R^5$ are one of the radicals mentioned under $R^6$; are hydrogen, $C_1$–$C_4$-alkylcarbonyl, $C_1$–$C_4$-haloalkylcarbonyl, $C_1$–$C_4$-alkoxycarbonyl, $C_1$–$C_4$-haloalkoxycarbonyl, $C_1$–$C_4$-alkylsulfonyl, $C_1$–$C_4$-haloalkylsulfonyl, $P(O)R^{11}R^{12}$ or $P(S)R^{11}R^{12}$; preferably $C_1$–$C_4$-alkylcarbonyl, $C_1$–$C_4$-haloalkylcarbonyl, $C_1$–$C_4$-alkylsulfonyl or $C_1$–$C_4$-haloalkylsulfonyl;

$R^6$ is $C_1$–$C_6$-alkyl, $C_3$–$C_6$-alkenyl or $C_3$–$C_6$-alkynyl, where the three abovementioned radicals may be partially or fully halogenated and/or may carry one to three of the following groups: cyano, $C_1$–$C_4$-alkoxy, $C_1$–$C_4$-haloalkoxy, $C_1$–$C_4$-alkylsulfonyl, $C_1$–$C_4$-haloalkylsulfonyl, $C_1$–$C_4$-alkylcarbonyl, $C_1$–$C_4$-alkoxycarbonyl and $C_1$–$C_4$-haloalkoxy-carbonyl;

is phenyl, phenyl-$C_1$–$C_4$-alkyl, heterocyclyl or heterocyclyl-$C_1$–$C_4$-alkyl, where the phenyl and the heterocyclyl radical of the four lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

is preferably $C_1$–$C_4$-alkyl, $C_3$–$C_6$-alkenyl or $C_3$–$C_6$-alkynyl, where the three abovementioned radicals may be partially or fully halogenated and/or may carry one to three of the following groups: cyano, $C_1$–$C_4$-alkoxy or $C_1$–$C_4$-alkoxycarbonyl;

$R^7$ is hydrogen or $C_1$–$C_4$-alkyl, such as methyl or ethyl;

$R^8$ is hydrogen, $C_1$–$C_6$-alkyl, $C_1$–$C_6$-alkoxycarbonyl or $C_1$–$C_6$-alkoxy; preferably hydrogen, $C_1$–$C_4$-alkyl or $C_1$–$C_4$-alkoxy;

$R^9$ is $C_1$–$C_6$-alkyl, $C_3$–$C_6$-alkenyl, $C_3$–$C_6$-alkynyl, $C_1$–$C_4$-alkylcarbonyl, $C_1$–$C_6$-alkoxy, $C_3$–$C_6$-alkenyloxy or $C_3$–$C_6$-alkynyloxy;

$R^{10}$ is hydrogen, $C_1$–$C_6$-alkyl, $C_3$–$C_6$-alkenyl or $C_3$–$C_6$-alkynyl;

$R^{11}$, $R^{12}$ are hydroxyl, $C_1$–$C_6$-alkyl or $C_1$–$C_6$-alkoxy;

$R^{13}$, $R^{14}$ are hydrogen, $C_1$–$C_6$-alkyl or $C_1$–$C_6$-haloalkyl; preferably hydrogen or $C_1$–$C_6$-alkyl, such as methyl, ethyl or propyl;

or $R^{13}$, $R^{14}$ together form a methylidene group which may be substituted by one or two substituents from the following group: halogen, cyano, $C_1$–$C_6$-alkyl, $C_1$–$C_6$-haloalkyl, $C_1$–$C_6$-alkoxy or $C_1$–$C_6$-haloalkoxy;

preferably ($R^{13}$, $R^{14}$) are hydrogen, $C_1$–$C_4$-alkyl such as methyl, ethyl or n-propyl or $C_1$–$C_4$-haloalkyl such as chloromethyl, fluoromethyl or trifluoromethyl; particularly preferably hydrogen, methyl or ethyl;

$R^{17}$ is hydroxyl, mercapto, halogen, $OR^{20}$, $SR^{20}$, $SOR^{21}$, $SO_2R^{21}$, $OSO_2R^{21}$, $OP(O)R^{22}R^{23}$, $OP(S)R^{22}R^{23}$, $NR^{24}R^{25}$, $ONR^{21}R^{21}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

preferably hydroxyl, mercapto, halogen, $OR^{20}$, $SR^{20}$, $SO_2R^{21}$, $OSO_2R^{21}$, $NR^{24}R^{25}$, $ONR^{21}R^{21}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$ is hydrogen or $C_1$–$C_4$-alkyl, such as methyl, ethyl or propyl or 1-methylethyl;
preferably methyl, ethyl, propyl or 1-methylethyl;
particularly preferably methyl or ethyl;

$R^{19}$ is hydrogen or $C_1$–$C_4$-alkyl, such as methyl, ethyl or propyl;
preferably hydrogen or methyl;
particularly preferably hydrogen;

$R^{20}$ is $C_1$–$C_6$-alkyl, $C_3$–$C_6$-alkenyl, $C_3$–$C_6$-haloalkenyl, $C_3$–$C_6$-alkynyl, $C_1$–$C_6$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N—($C_3$–$C_6$-alkenyl)-N—($C_1$–$C_6$-alkyl)aminocarbonyl, N—($C_3$–$C_6$-alkynyl)-N—($C_1$–$C_6$-alkyl)aminocarbonyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl, N—($C_3$–$C_6$-alkynyl)-N—($C_1$–$C_6$-alkoxy)aminocarbonyl, di-($C_1$–$C_6$-alkyl)aminothiocarbonyl, $C_1$–$C_6$-alkoxyimino-$C_1$–$C_6$-alkyl, where the abovementioned alkyl, cycloalkyl or alkoxy radicals may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, hydroxycarbonyl, $C_1$–$C_4$-alkylaminocarbonyl, di-($C_1$–$C_4$-alkyl)aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxy-thiocarbonyl or heterocyclyl-$C_1$–$C_6$-alkenylcarbonyl, where the phenyl or the heterocyclyl radical of the 14 last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

is preferably $C_1$–$C_6$-alkyl, $C_3$–$C_6$-alkenyl, $C_3$–$C_6$-alkynyl, $C_1$–$C_6$-alkylcarbonyl, $C_1$–$C_6$-alkoxycarbonyl, $C_1$–$C_6$-alkyl-aminocarbonyl or N,N-di($C_1$–$C_6$-alkyl)aminocarbonyl, where the abovementioned alkyl or alkoxy radicals may be partially or fully halogenated and/or may carry one to three of the following groups: cyano, $C_1$–$C_4$-alkoxy, $C_1$–$C_4$-alkylthio or $C_1$–$C_4$-alkoxycarbonyl;

is phenyl, phenyl-$C_1$–$C_6$-alkyl, phenylcarbonyl-$C_1$–$C_6$-alkyl, phenylcarbonyl, phenoxycarbonyl, heterocyclyl, heterocyclyl-$C_1$–$C_6$-alkyl, heterocyclylcarbonyl-$C_1$–$C_6$-alkyl, heterocyclylcarbonyl or heterocyclyloxycarbonyl, where the phenyl or the heterocyclyl radical of the 10 last-mentioned substituents may be partially or fully halogenated and/or may carry one to three of the following radicals: nitro, cyano, $C_1$–$C_4$-alkyl $C_1$–$C_4$-haloalkyl, $C_1$–$C_4$-alkoxy or $C_1$–$C_4$-haloalkoxy;

$R^{21}$ is $C_1$–$C_6$-alkyl, $C_3$–$C_6$-alkenyl or $C_3$–$C_6$-cycloalkyl, where the three abovementioned radicals may be partially or fully halogenated and/or may carry one to three of the following groups: cyano, $C_1$–$C_4$-alkoxy, $C_1$–$C_4$-alkylthio, $C_1$–$C_4$-alkylcarbonyl or $C_1$–$C_4$-alkoxycarbonyl;

is phenyl, phenyl-$C_1$–$C_4$-alkyl, heterocyclyl or heterocyclyl-$C_1$–$C_4$-alkyl, where the phenyl or the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{22}$, $R^{23}$ are hydroxyl, $C_1$–$C_6$-alkyl, $C_1$–$C_6$-alkoxy, phenyl, phenyl-$C_1$–$C_4$-alkyl or phenoxy, where the three last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{24}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the abovementioned alkyl, cycloalkyl or alkoxy radicals may be partially or fully halogenated and/or may carry one to three of the following radicals: cyano, $C_1$–$C_4$-alkoxycarbonyl, $C_1$–$C_4$-alkylaminocarbonyl, di-($C_1$–$C_4$-alkyl) aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{25}$ is $C_1$–$C_6$-alkyl or $C_3$–$C_6$-alkenyl.

Very particularly preference is given to compounds of the formula I, where $R^1$ is cyano, thiocyanato, nitro, $OR^4$, $SO_2R^6$, $ONR^6R^7$, $ON=CR^6R^7$, $NR^9R^{10}$, $P(O)R^{11}R^{12}$, $P(S)R^{11}R^{12}$, $COR^6$, $CO_2R^6$ or N-bonded heterocyclyl;

$R^4$ is $C_1$–$C_6$-haloalkyl, $C_3$–$C_6$-alkenyl, $C_3$–$C_6$-alkynyl, where the three abovementioned radicals may be partially or fully halogenated and/or may carry one to three of the following groups: cyano, $C_1$–$C_4$-alkoxy, $C_1$–$C_4$-haloalkoxy, $C_1$–$C_4$-alkylsulfonyl, $C_1$–$C_4$-haloalkylsulfonyl, $C_1$–$C_4$-alkylcarbonyl, $C_1$–$C_4$-alkoxycarbonyl or $C_1$–$C_4$-haloalkoxycarbonyl;

is $C_1$–$C_4$-alkylcarbonyl, $C_1$–$C_4$-haloalkylcarbonyl, $C_1$–$C_4$-alkoxycarbonyl, $C_1$–$C_4$-haloalkoxycarbonyl, $C_1$–$C_4$-alkylsulfonyl, $C_1$–$C_4$-haloalkylsulfonyl, $P(O)R^1R^{11}R^{12}$ or $P(S)R^{11}R^{12}$;

is phenyl, phenyl-$C_1$–$C_4$-alkyl, heterocyclyl or heterocyclyl-(C–$C_4$-alkyl, where the phenyl and the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl.

Very particular preference is also given to the compounds of the formula I, where $R^1$ is cyano, thiocyanato, nitro, $SR^5$, $SO_2R^6$, $ONR^6R^7$, $ON=CR^6R^8$, $NR^9R^{10}$, $P(O)R^{11}R^{12}$, $P(S)R^{11}R^{12}$, $COR^6$, $C_{O2}R^6$ or N-bonded heterocyclyl.

Very particular preference is also given to the compounds of the formula I, where $R^{17}$ is hydroxyl.

Very particular preference is also given to the compounds of the formula I, where $R^{17}$ is halogen, $OR^{20}$, $SR^{20}$, $SO_2R^{21}$, $OSO_2R^{21}$, $NR^{24}R^{25}$, $ONR^{21}R^{21}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy.

Likewise, very particular preference is given to the compounds of the formula I, where $R^{18}$ is $C_1$–$C_4$-alkyl;

$R^{19}$ is hydrogen or $C_1$–$C_4$-alkyl.

Likewise, very particular preference is given to the compounds of the formula I, where A is $C_1$–$C_6$-alkanediyl; particularly preferably methanediyl;

$R^1$ is $NO_2$, $OR^4$, $SR^5$, $SOR^6$, $SO_2R^6$, $NR^9R^{10}$, $P(O)R^{11}R^{12}$ or N-bonded heterocyclyl;

particularly preferably $OR^4$, $SR^5$, $SOR^6$, $SO_2R^6$, $P(O)R^{11}R^{12}$ or N-bonded heterocyclyl;

with particular preference $OR^4$, $SR^5$, $SOR^6$, $SO_2R^6$, or $P(O)R^{11}R^{12}$;

likewise with particular preference $SR^5$ or $SO_2R^6$;

likewise with particular preference $OR^4$;

$R^3$ is hydrogen;

X is $CR^{13}R^{14}$, C=O or $SO_2$;

particularly preferably $CR^{13}R^{14}$;

m is 2;

n is 0;

$R^4$ is $C_1$–$C_6$-alkyl which may be partially or fully halogenated;

$R^5$ is $C_1$–$C_6$-alkyl, $C_3$–$C_6$-alkenyl or heterocyclyl; particularly preferably $C_1$–$C_6$-alkyl or heterocyclyl; with particular preference $C_1$–$C_6$-alkyl;

$R^6$ is $C_1$–$C_6$-alkyl which may be partially or fully halogenated; particularly preferably $C_1$–$C_6$-alkyl;

$R^9$ is $C_1$–$C_6$-alkyl, $C_3$–$C_6$-alkenyl or $C_1$–$C_4$-haloalkylcarbonyl;

$R^{10}$ is $C_1$–$C_6$-alkyl or $C_3$–$C_6$-alkenyl;

$R^{11}$, $R^{12}$ are $C_1$–$C_6$-alkyl;

$R^{17}$ hydroxyl;

$R^{18}$ is $C_1$–$C_6$-alkyl;

$R^{19}$ is hydrogen or $C_1$–$C_6$-alkyl;

particularly preferably hydrogen.

Likewise, very particular preference is given to the compounds of the formula Ia.

Most preference is given to the compounds of the formula Ia (=I, where $R^3$, $R^{19}$=H, $R^{17}$=OH, $R^{18}$=$CH_3$, m=2, n=0), in particular to the compounds Ia1.1 to Ia1.285, where the radical definitions $R^1$ to $R^{23}$, A, X, m and n are of particular importance for the compounds according to the invention not only in combination with one another, but in each case also on their own.

TABLE 1

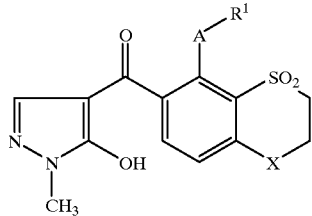

Ia1

| No. | A | $R^1$ | X |
|---|---|---|---|
| Ia1.1 | $CH_2$ | $NO_2$ | $SO_2$ |
| Ia1.2 | $CH_2$ | $OCH_3$ | $SO_2$ |
| Ia1.3 | $CH_2$ | $OCH_2CH_3$ | $SO_2$ |
| Ia1.4 | $CH_2$ | $O(CH_2)_2CH_3$ | $SO_2$ |
| Ia1.5 | $CH_2$ | $O(CH_2)_3CH_3$ | $SO_2$ |
| Ia1.6 | $CH_2$ | $OCH(CH_3)_2$ | $SO_2$ |
| Ia1.7 | $CH_2$ | $OCH(CH_3)CH_2CH_3$ | $SO_2$ |
| Ia1.8 | $CH_2$ | $OCH_2CH(CH_3)_2$ | $SO_2$ |
| Ia1.9 | $CH_2$ | $OC(CH_3)_3$ | $SO_2$ |
| Ia1.10 | $CH_2$ | $OCH_2CH=CH_2$ | $SO_2$ |
| Ia1.11 | $CH_2$ | $OCH_2CH=CH-CH_3$ | $SO_2$ |
| Ia1.12 | $CH_2$ | $OCH(CH_3)CH=CH_2$ | $SO_2$ |
| Ia1.13 | $CH_2$ | $OCH_2C\equiv CH$ | $SO_2$ |
| Ia1.14 | $CH_2$ | $OCH(CH_3)C\equiv CH$ | $SO_2$ |
| Ia1.15 | $CH_2$ | $OCH_2C\equiv C-CH_3$ | $SO_2$ |
| Ia1.16 | $CH_2$ | $OCH_2F$ | $SO_2$ |
| Ia1.17 | $CH_2$ | $OCH_2Cl$ | $SO_2$ |
| Ia1.18 | $CH_2$ | $OCF_3$ | $SO_2$ |
| Ia1.19 | $CH_2$ | $OCHF_2$ | $SO_2$ |
| Ia1.20 | $CH_2$ | $OCH_2CH_2F$ | $SO_2$ |
| Ia1.21 | $CH_2$ | $OCH_2CH_2Cl$ | $SO_2$ |
| Ia1.22 | $CH_2$ | $OCH_2CF_3$ | $SO_2$ |
| Ia1.23 | $CH_2$ | $OCH_2CCl_3$ | $SO_2$ |
| Ia1.24 | $CH_2$ | $OCH_2CN$ | $SO_2$ |
| Ia1.25 | $CH_2$ | $OCH(CH_3)CN$ | $SO_2$ |
| Ia1.26 | $CH_2$ | $OCH_2C_6H_5$ | $SO_2$ |
| Ia1.27 | $CH_2$ | $OCH_2(furan-2-yl)$ | $SO_2$ |
| Ia1.28 | $CH_2$ | $OCH_2(furan-3-yl)$ | $SO_2$ |
| Ia1.29 | $CH_2$ | $SCH_3$ | $SO_2$ |
| Ia1.30 | $CH_2$ | $SCH_2CH_3$ | $SO_2$ |
| Ia1.31 | $CH_2$ | $S(CH_2)_2CH_3$ | $SO_2$ |
| Ia1.32 | $CH_2$ | $S(CH_2)_3CH_3$ | $SO_2$ |
| Ia1.33 | $CH_2$ | $SCH(CH_3)_2$ | $SO_2$ |
| Ia1.34 | $CH_2$ | $SCH_2CH(CH_3)_2$ | $SO_2$ |
| Ia1.35 | $CH_2$ | $SCH_2CH=CH_2$ | $SO_2$ |
| Ia1.36 | $CH_2$ | $SCH_2C\equiv CH$ | $SO_2$ |
| Ia1.37 | $CH_2$ | $SC_6H_5$ | $SO_2$ |
| Ia1.38 | $CH_2$ | $S(4-CH_3-C_6H_4)$ | $SO_2$ |
| Ia1.39 | $CH_2$ | $S(4-Cl-C_6H_4)$ | $SO_2$ |
| Ia1.40 | $CH_2$ | $SO_2CH_3$ | $SO_2$ |
| Ia1.41 | $CH_2$ | $SO_2CH_2CH_3$ | $SO_2$ |
| Ia1.42 | $CH_2$ | $SO_2(CH_2)_2CH_3$ | $SO_2$ |
| Ia1.43 | $CH_2$ | $SO_2(CH_2)_3CH_3$ | $SO_2$ |
| Ia1.44 | $CH_2$ | $SO_2CH(CH_3)_2$ | $SO_2$ |
| Ia1.45 | $CH_2$ | $SO_2CH_2CH(CH_3)_2$ | $SO_2$ |
| Ia1.46 | $CH_2$ | $SO_2CH_2CH=CH_2$ | $SO_2$ |
| Ia1.47 | $CH_2$ | $SO_2CH_2C\equiv CH$ | $SO_2$ |
| Ia1.48 | $CH_2$ | $SO_2C_6H_5$ | $SO_2$ |
| Ia1.49 | $CH_2$ | $SO_2(4-CH_3-C_6H_4)$ | $SO_2$ |
| Ia1.50 | $CH_2$ | $SO_2(4-Cl-C_6H_4)$ | $SO_2$ |
| Ia1.51 | $CH_2$ | $SO_2CF_3$ | $SO_2$ |
| Ia1.52 | $CH_2$ | $N(OCH_3)CH_3$ | $SO_2$ |
| Ia1.53 | $CH_2$ | $P(O)(OCH_3)_2$ | $SO_2$ |
| Ia1.54 | $CH_2$ | $P(O)(OCH_2CH_3)_2$ | $SO_2$ |
| Ia1.55 | $CH_2$ | $P(O)(OC_6H_5)_2$ | $SO_2$ |
| Ia1.56 | $CH_2$ | $P(O)(CH_3)_2$ | $SO_2$ |
| Ia1.57 | $CH_2$ | $P(O)(CH_2CH_3)_2$ | $SO_2$ |

TABLE 1-continued

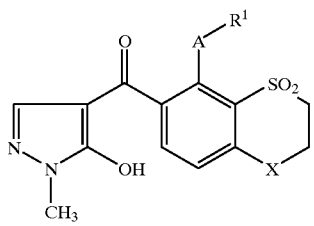

Ia1

| No. | A | $R^1$ | X |
|---|---|---|---|
| Ia1.58 | $CH_2$ | $P(O)(C_6H_5)_2$ | $SO_2$ |
| Ia1.59 | $CH_2$ | $P(S)(OCH_3)_2$ | $SO_2$ |
| Ia1.60 | $CH_2$ | $P(S)(OCH_2CH_3)_2$ | $SO_2$ |
| Ia1.61 | $CH_2$ | thien-2-yl | $SO_2$ |
| Ia1.62 | $CH_2$ | morpholin-4-yl | $SO_2$ |
| Ia1.63 | $CH_2$ | tetrahydroisoxazol-2-yl | $SO_2$ |
| Ia1.64 | $CH_2$ | pyrrolidin-1-yl | $SO_2$ |
| Ia1.65 | $CH_2$ | imidazol-1-yl | $SO_2$ |
| Ia1.66 | $CH_2$ | pyrazol-1-yl | $SO_2$ |
| Ia1.67 | $CH_2$ | 1,2,4-triazol-1-yl | $SO_2$ |
| Ia1.68 | $CH_2$ | $NO_2$ | $C(CH_3)_2$ |
| Ia1.69 | $CH_2$ | $OCH_3$ | $C(CH_3)_2$ |
| Ia1.70 | $CH_2$ | $OCH_2CH_3$ | $C(CH_3)_2$ |
| Ia1.71 | $CH_2$ | $O(CH_2)_2CH_3$ | $C(CH_3)_2$ |
| Ia1.72 | $CH_2$ | $O(CH_2)_3CH_3$ | $C(CH_3)_2$ |
| Ia1.73 | $CH_2$ | $OCH(CH_3)_2$ | $C(CH_3)_2$ |
| Ia1.74 | $CH_2$ | $OCH(CH_3)CH_2CH_3$ | $C(CH_3)_2$ |
| Ia1.75 | $CH_2$ | $OCH_2CH(CH_3)_2$ | $C(CH_3)_2$ |
| Ia1.76 | $CH_2$ | $OC(CH_3)_3$ | $C(CH_3)_2$ |
| Ia1.77 | $CH_2$ | $OCH_2CH=CH_2$ | $C(CH_3)_2$ |
| Ia1.78 | $CH_2$ | $OCH_2CH=CH-CH_3$ | $C(CH_3)_2$ |
| Ia1.79 | $CH_2$ | $OCH(CH_3)CH=CH_2$ | $C(CH_3)_2$ |
| Ia1.80 | $CH_2$ | $OCH_2C\equiv CH$ | $C(CH_3)_2$ |
| Ia1.81 | $CH_2$ | $OCH(CH_3)C\equiv CH$ | $C(CH_3)_2$ |
| Ia1.82 | $CH_2$ | $OCH_2C\equiv C-CH_3$ | $C(CH_3)_2$ |
| Ia1.83 | $CH_2$ | $OCH_2F$ | $C(CH_3)_2$ |
| Ia1.84 | $CH_2$ | $OCH_2Cl$ | $C(CH_3)_2$ |
| Ia1.85 | $CH_2$ | $OCF_3$ | $C(CH_3)_2$ |
| Ia1.86 | $CH_2$ | $OCHF_2$ | $C(CH_3)_2$ |
| Ia1.87 | $CH_2$ | $OCH_2CH_2F$ | $C(CH_3)_2$ |
| Ia1.88 | $CH_2$ | $OCH_2CH_2Cl$ | $C(CH_3)_2$ |
| Ia1.89 | $CH_2$ | $OCH_2CF_3$ | $C(CH_3)_2$ |
| Ia1.90 | $CH_2$ | $OCH_2CCl_3$ | $C(CH_3)_2$ |
| Ia1.91 | $CH_2$ | $OCH_2CN$ | $C(CH_3)_2$ |
| Ia1.92 | $CH_2$ | $OCH(CH_3)CN$ | $C(CH_3)_2$ |
| Ia1.93 | $CH_2$ | $OCH_2C_6H_5$ | $C(CH_3)_2$ |
| Ia1.94 | $CH_2$ | $OCH_2(furan-2-yl)$ | $C(CH_3)_2$ |
| Ia1.95 | $CH_2$ | $OCH_2(furan-3-yl)$ | $C(CH_3)_2$ |
| Ia1.96 | $CH_2$ | $SCH_3$ | $C(CH_3)_2$ |
| Ia1.97 | $CH_2$ | $SCH_2CH_3$ | $C(CH_3)_2$ |
| Ia1.98 | $CH_2$ | $S(CH_2)_2CH_3$ | $C(CH_3)_2$ |
| Ia1.99 | $CH_2$ | $S(CH_2)_3CH_3$ | $C(CH_3)_2$ |
| Ia1.100 | $CH_2$ | $SCH(CH_3)_2$ | $C(CH_3)_2$ |
| Ia1.101 | $CH_2$ | $SCH_2CH(CH_3)_2$ | $C(CH_3)_2$ |
| Ia1.102 | $CH_2$ | $SCH_2CH=CH_2$ | $C(CH_3)_2$ |
| Ia1.103 | $CH_2$ | $SCH_2C\equiv CH$ | $C(CH_3)_2$ |
| Ia1.104 | $CH_2$ | $SC_6H_5$ | $C(CH_3)_2$ |
| Ia1.105 | $CH_2$ | $S(4-CH_3-C_6H_4)$ | $C(CH_3)_2$ |
| Ia1.106 | $CH_2$ | $S(4-Cl-C_6H_4)$ | $C(CH_3)_2$ |
| Ia1.107 | $CH_2$ | $SO_2CH_3$ | $C(CH_3)_2$ |
| Ia1.108 | $CH_2$ | $SO_2CH_2CH_3$ | $C(CH_3)_2$ |
| Ia1.109 | $CH_2$ | $SO_2(CH_2)_2CH_3$ | $C(CH_3)_2$ |
| Ia1.110 | $CH_2$ | $SO_2(CH_2)_3CH_3$ | $C(CH_3)_2$ |
| Ia1.111 | $CH_2$ | $SO_2CH(CH_3)_2$ | $C(CH_3)_2$ |
| Ia1.112 | $CH_2$ | $SO_2CH_2CH(CH_3)_2$ | $C(CH_3)_2$ |
| Ia1.113 | $CH_2$ | $SO_2CH_2CH=CH_2$ | $C(CH_3)_2$ |
| Ia1.114 | $CH_2$ | $SO_2CH_2C\equiv CH$ | $C(CH_3)_2$ |
| Ia1.115 | $CH_2$ | $SO_2C_6H_5$ | $C(CH_3)_2$ |
| Ia1.116 | $CH_2$ | $SO_2(4-CH_3-C_6H_4)$ | $C(CH_3)_2$ |
| Ia1.117 | $CH_2$ | $SO_2(4-Cl-C_6H_4)$ | $C(CH_3)_2$ |
| Ia1.118 | $CH_2$ | $SO_2CF_3$ | $C(CH_3)_2$ |
| Ia1.119 | $CH_2$ | $N(OCH_3)CH_3$ | $C(CH_3)_2$ |
| Ia1.120 | $CH_2$ | $P(O)(OCH_3)_2$ | $C(CH_3)_2$ |
| Ia1.121 | $CH_2$ | $P(O)(OCH_2CH_3)_2$ | $C(CH_3)_2$ |

TABLE 1-continued

Ia1

| No. | A | R¹ | X |
|---|---|---|---|
| Ia1.122 | $CH_2$ | $P(O)(OC_6H_5)_2$ | $C(CH_3)_2$ |
| Ia1.123 | $CH_2$ | $P(O)(CH_3)_2$ | $C(CH_3)_2$ |
| Ia1.124 | $CH_2$ | $P(O)(CH_2CH_3)_2$ | $C(CH_3)_2$ |
| Ia1.125 | $CH_2$ | $P(O)(C_6H_5)_2$ | $C(CH_3)_2$ |
| Ia1.126 | $CH_2$ | $P(S)(OCH_3)_2$ | $C(CH_3)_2$ |
| Ia1.127 | $CH_2$ | $P(S)(OCH_2CH_3)_2$ | $C(CH_3)_2$ |
| Ia1.128 | $CH_2$ | thien-2-yl | $C(CH_3)_2$ |
| Ia1.129 | $CH_2$ | morpholin-4-yl | $C(CH_3)_2$ |
| Ia1.130 | $CH_2$ | tetrahydroisoxazol-2-yl | $C(CH_3)_2$ |
| Ia1.131 | $CH_2$ | pyrrolidin-1-yl | $C(CH_3)_2$ |
| Ia1.132 | $CH_2$ | imidazol-1-yl | $C(CH_3)_2$ |
| Ia1.133 | $CH_2$ | pyrazol-1-yl | $C(CH_3)_2$ |
| Ia1.134 | $CH_2$ | 1,2,4-triazol-1-yl | $C(CH_3)_2$ |
| Ia1.135 | $CH_2$ | $NO_2$ | C=O |
| Ia1.136 | $CH_2$ | $OCH_3$ | C=O |
| Ia1.137 | $CH_2$ | $OCH_2CH_3$ | C=O |
| Ia1.138 | $CH_2$ | $O(CH_2)_2CH_3$ | C=O |
| Ia1.139 | $CH_2$ | $O(CH_2)_3CH_3$ | C=O |
| Ia1.140 | $CH_2$ | $OCH(CH_3)_2$ | C=O |
| Ia1.141 | $CH_2$ | $OCH(CH_3)CH_2CH_3$ | C=O |
| Ia1.142 | $CH_2$ | $OCH_2CH(CH_3)_2$ | C=O |
| Ia1.143 | $CH_2$ | $OC(CH_3)_3$ | C=O |
| Ia1.144 | $CH_2$ | $OCH_2CH=CH_2$ | C=O |
| Ia1.145 | $CH_2$ | $OCH_2CH=CH-CH_3$ | C=O |
| Ia1.146 | $CH_2$ | $OCH(CH_3)CH=CH_2$ | C=O |
| Ia1.147 | $CH_2$ | $OCH_2C\equiv CH$ | C=O |
| Ia1.148 | $CH_2$ | $OCH(CH_3)C\equiv CH$ | C=O |
| Ia1.149 | $CH_2$ | $OCH_2C\equiv C-CH_3$ | C=O |
| Ia1.150 | $CH_2$ | $OCH_2F$ | C=O |
| Ia1.151 | $CH_2$ | $OCH_2Cl$ | C=O |
| Ia1.152 | $CH_2$ | $OCF_3$ | C=O |
| Ia1.153 | $CH_2$ | $OCHF_2$ | C=O |
| Ia1.154 | $CH_2$ | $OCH_2CH_2F$ | C=O |
| Ia1.155 | $CH_2$ | $OCH_2CH_2Cl$ | C=O |
| Ia1.156 | $CH_2$ | $OCH_2CF_3$ | C=O |
| Ia1.157 | $CH_2$ | $OCH_2CCl_3$ | C=O |
| Ia1.158 | $CH_2$ | $OCH_2CN$ | C=O |
| Ia1.159 | $CH_2$ | $OCH(CH_3)CN$ | C=O |
| Ia1.160 | $CH_2$ | $OCH_2C_6H_5$ | C=O |
| Ia1.161 | $CH_2$ | $OCH_2$(furan-2-yl) | C=O |
| Ia1.162 | $CH_2$ | $OCH_2$(furan-3-yl) | C=O |
| Ia1.163 | $CH_2$ | $SCH_3$ | C=O |
| Ia1.164 | $CH_2$ | $SCH_2CH_3$ | C=O |
| Ia1.165 | $CH_2$ | $S(CH_2)_2CH_3$ | C=O |
| Ia1.166 | $CH_2$ | $S(CH_2)_3CH_3$ | C=O |
| Ia1.167 | $CH_2$ | $SCH(CH_3)_2$ | C=O |
| Ia1.168 | $CH_2$ | $SCH_2CH(CH_3)_2$ | C=O |
| Ia1.169 | $CH_2$ | $SCH_2CH=CH_2$ | C=O |
| Ia1.170 | $CH_2$ | $SCH_2C\equiv CH$ | C=O |
| Ia1.171 | $CH_2$ | $SC_6H_5$ | C=O |
| Ia1.172 | $CH_2$ | $S(4-CH_3-C_6H_4)$ | C=O |
| Ia1.173 | $CH_2$ | $S(4-Cl-C_6H_4)$ | C=O |
| Ia1.174 | $CH_2$ | $SO_2CH_3$ | C=O |
| Ia1.175 | $CH_2$ | $SO_2CH_2CH_3$ | C=O |
| Ia1.176 | $CH_2$ | $SO_2(CH_2)_2CH_3$ | C=O |
| Ia1.177 | $CH_2$ | $SO_2(CH_2)_3CH_3$ | C=O |
| Ia1.178 | $CH_2$ | $SO_2CH(CH_3)_2$ | C=O |
| Ia1.179 | $CH_2$ | $SO_2CH_2CH(CH_3)_2$ | C=O |
| Ia1.180 | $CH_2$ | $SO_2CH_2CH=CH_2$ | C=O |
| Ia1.181 | $CH_2$ | $SO_2CH_2C\equiv CH$ | C=O |
| Ia1.182 | $CH_2$ | $SO_2C_6H_5$ | C=O |
| Ia1.183 | $CH_2$ | $SO_2(4-CH_3-C_6H_4)$ | C=O |
| Ia1.184 | $CH_2$ | $SO_2(4-Cl-C_6H_4)$ | C=O |
| Ia1.185 | $CH_2$ | $SO_2CF_3$ | C=O |
| Ia1.186 | $CH_2$ | $N(OCH_3)CH_3$ | C=O |
| Ia1.187 | $CH_2$ | $P(O)(OCH_3)_2$ | C=O |
| Ia1.188 | $CH_2$ | $P(O)(OCH_2CH_3)_2$ | C=O |
| Ia1.189 | $CH_2$ | $P(O)(OC_6H_5)_2$ | C=O |
| Ia1.190 | $CH_2$ | $P(O)(CH_3)_2$ | C=O |
| Ia1.191 | $CH_2$ | $P(O)(CH_2CH_3)_2$ | C=O |
| Ia1.192 | $CH_2$ | $P(O)(C_6H_5)_2$ | C=O |
| Ia1.193 | $CH_2$ | $P(S)(OCH_3)_2$ | C=O |
| Ia1.194 | $CH_2$ | $P(S)(OCH_2CH_3)_2$ | C=O |
| Ia1.195 | $CH_2$ | thien-2-yl | C=O |
| Ia1.196 | $CH_2$ | morpholin-4-yl | C=O |
| Ia1.197 | $CH_2$ | tetrahydroisoxazol-2-yl | C=O |
| Ia1.198 | $CH_2$ | pyrrolidin-1-yl | C=O |
| Ia1.199 | $CH_2$ | imidazol-1-yl | C=O |
| Ia1.200 | $CH_2$ | pyrazol-1-yl | C=O |
| Ia1.201 | $CH_2$ | 1,2,4-triazol-1-yl | C=O |
| Ia1.202 | CH=CH | CN | $SO_2$ |
| Ia1.203 | CH=CH | $NO_2$ | $SO_2$ |
| Ia1.204 | CH=CH | $SO_2CH_3$ | $SO_2$ |
| Ia1.205 | CH=CH | $SO_2CH_2CH_3$ | $SO_2$ |
| Ia1.206 | CH=CH | $SO_2(CH_2)_2CH_3$ | $SO_2$ |
| Ia1.207 | CH=CH | $SO_2(CH_2)_3CH_3$ | $SO_2$ |
| Ia1.208 | CH=CH | $SO_2CH(CH_3)_2$ | $SO_2$ |
| Ia1.209 | CH=CH | $SO_2CH_2CH(CH_3)_2$ | $SO_2$ |
| Ia1.210 | CH=CH | $COCH_3$ | $SO_2$ |
| Ia1.211 | CH=CH | $COCH_2CH_3$ | $SO_2$ |
| Ia1.212 | CH=CH | $COCH_2F$ | $SO_2$ |
| Ia1.213 | CH=CH | $COCH_2Cl$ | $SO_2$ |
| Ia1.214 | CH=CH | $COCH_2Br$ | $SO_2$ |
| Ia1.215 | CH=CH | $COCF_3$ | $SO_2$ |
| Ia1.216 | CH=CH | $COCHF_2$ | $SO_2$ |
| Ia1.217 | CH=CH | $CO_2CH_3$ | $SO_2$ |
| Ia1.218 | CH=CH | $CO_2CH_2CH_3$ | $SO_2$ |
| Ia1.219 | CH=CH | $CO_2(CH)_2CH_3$ | $SO_2$ |
| Ia1.220 | CH=CH | $CO_2(CH_2)_3CH_3$ | $SO_2$ |
| Ia1.221 | CH=CH | $CO_2CH(CH_3)_2$ | $SO_2$ |
| Ia1.222 | CH=CH | $CO_2CH_2CH(CH_3)_2$ | $SO_2$ |
| Ia1.223 | CH=CH | $CO_2CH_2CH_2F$ | $SO_2$ |
| Ia1.224 | CH=CH | $CO_2CH_2CH_2Cl$ | $SO_2$ |
| Ia1.225 | CH=CH | $CO_2CH_2CF_3$ | $SO_2$ |
| Ia1.226 | CH=CH | $CO_2CH_2CCl_3$ | $SO_2$ |
| Ia1.227 | CH=CH | $CO_2C_6H_5$ | $SO_2$ |
| Ia1.228 | CH=CH | furan-2-yl | $SO_2$ |
| Ia1.229 | CH=CH | thien-2-yl | $SO_2$ |
| Ia1.230 | CH=CH | CN | $C(CH_3)_2$ |
| Ia1.231 | CH=CH | $NO_2$ | $C(CH_3)_2$ |
| Ia1.232 | CH=CH | $SO_2CH_3$ | $C(CH_3)_2$ |
| Ia1.233 | CH=CH | $SO_2CH_2CH_3$ | $C(CH_3)_2$ |
| Ia1.234 | CH=CH | $SO_2(CH_2)_2CH_3$ | $C(CH_3)_2$ |
| Ia1.235 | CH=CH | $SO_2(CH_2)_3CH_3$ | $C(CH_3)_2$ |
| Ia1.236 | CH=CH | $SO_2CH(CH_3)_2$ | $C(CH_3)_2$ |
| Ia1.237 | CH=CH | $SO_2CH_2CH(CH_3)_2$ | $C(CH_3)_2$ |
| Ia1.238 | CH=CH | $COCH_3$ | $C(CH_3)_2$ |
| Ia1.239 | CH=CH | $COCH_2CH_3$ | $C(CH_3)_2$ |
| Ia1.240 | CH=CH | $COCH_2F$ | $C(CH_3)_2$ |
| Ia1.241 | CH=CH | $COCH_2Cl$ | $C(CH_3)_2$ |
| Ia1.242 | CH=CH | $COCH_2Br$ | $C(CH_3)_2$ |
| Ia1.243 | CH=CH | $COCF_3$ | $C(CH_3)_2$ |
| Ia1.244 | CH=CH | $COCHF_2$ | $C(CH_3)_2$ |
| Ia1.245 | CH=CH | $CO_2CH_3$ | $C(CH_3)_2$ |
| Ia1.246 | CH=CH | $CO_2CH_2CH_3$ | $C(CH_3)_2$ |
| Ia1.247 | CH=CH | $CO_2(CH)_2CH_3$ | $C(CH_3)_2$ |
| Ia1.248 | CH=CH | $CO_2(CH_2)_3CH_3$ | $C(CH_3)_2$ |
| Ia1.249 | CH=CH | $CO_2CH(CH_3)_2$ | $C(CH_3)_2$ |

TABLE 1-continued

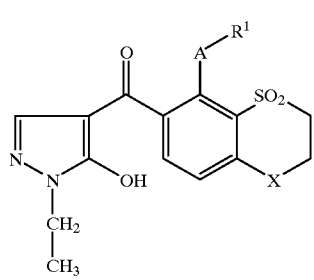

Ia1

| No. | A | R¹ | X |
|---|---|---|---|
| Ia1.250 | CH=CH | CO₂CH₂CH(CH₃)₂ | C(CH₃)₂ |
| Ia1.251 | CH=CH | CO₂CH₂CH₂F | C(CH₃)₂ |
| Ia1.252 | CH=CH | CO₂CH₂CH₂Cl | C(CH₃)₂ |
| Ia1.253 | CH=CH | CO₂CH₂CF₃ | C(CH₃)₂ |
| Ia1.254 | CH=CH | CO₂CH₂CCl₃ | C(CH₃)₂ |
| Ia1.255 | CH=CH | CO₂C₆H₅ | C(CH₃)₂ |
| Ia1.256 | CH=CH | furan-2-yl | C(CH₃)₂ |
| Ia1.257 | CH=CH | thien-2-yl | C(CH₃)₂ |
| Ia1.258 | CH=CH | CN | C=O |
| Ia1.259 | CH=CH | NO₂ | C=O |
| Ia1.260 | CH=CH | SO₂CH₃ | C=O |
| Ia1.261 | CH=CH | SO₂CH₂CH₃ | C=O |
| Ia1.262 | CH=CH | SO₂(CH₂)₂CH₃ | C=O |
| Ia1.263 | CH=CH | SO₂(CH₂)₃CH₃ | C=O |
| Ia1.264 | CH=CH | SO₂CH(CH₃)₂ | C=O |
| Ia1.265 | CH=CH | SO₂CH₂CH(CH₃)₂ | C=O |
| Ia1.266 | CH=CH | COCH₃ | C=O |
| Ia1.267 | CH=CH | COCH₂CH₃ | C=O |
| Ia1.268 | CH=CH | COCH₂F | C=O |
| Ia1.269 | CH=CH | COCH₂Cl | C=O |
| Ia1.270 | CH=CH | COCH₂Br | C=O |
| Ia1.271 | CH=CH | COCF₃ | C=O |
| Ia1.272 | CH=CH | COCHF₂ | C=O |
| Ia1.273 | CH=CH | CO₂CH₃ | C=O |
| Ia1.274 | CH=CH | CO₂CH₂CH₃ | C=O |
| Ia1.275 | CH=CH | CO₂(CH)₂CH₃ | C=O |
| Ia1.276 | CH=CH | CO₂(CH₂)₃CH₃ | C=O |
| Ia1.277 | CH=CH | CO₂CH(CH₃)₂ | C=O |
| Ia1.278 | CH=CH | CO₂CH₂CH(CH₃)₂ | C=O |
| Ia1.279 | CH=CH | CO₂CH₂CH₂F | C=O |
| Ia1.280 | CH=CH | CO₂CH₂CH₂Cl | C=O |
| Ia1.281 | CH=CH | CO₂CH₂CF₃ | C=O |
| Ia1.282 | CH=CH | CO₂CH₂CCl₃ | C=O |
| Ia1.283 | CH=CH | CO₂C₆H₅ | C=O |
| Ia1.284 | CH=CH | furan-2-yl | C=O |
| Ia1.285 | CH=CH | thien-2-yl | C=O |

Most preference is furthermore given to the following thiochromanoylpyrazolone derivatives of the formula I:

the compounds of the formula Ia2, in particular the compounds Ia2.1 to Ia2.285, which differ from the compounds Ia1.1 to Ia1.285 in that $R^{18}$ is ethyl.

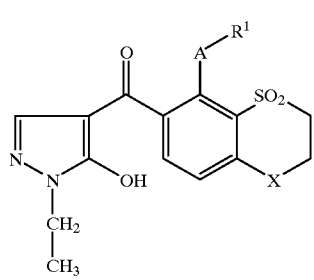

Ia2

The compounds of the formula Ia3, in particular the compounds Ia3.1 to Ia3.285, which differ from the compounds Ia1.1 to Ia1.285 in that $R^8$ is propyl.

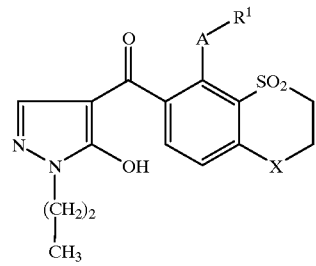

Ia3

The compounds of the formula Ia4, in particular the compounds Ia4.1 to Ia4.285, which differ from the compounds Ia1.1 to Ia1.285 in that $R^{19}$ is methyl.

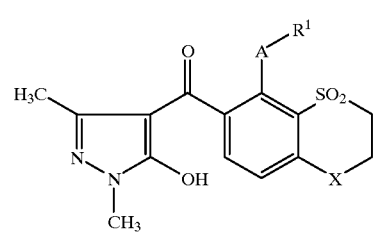

Ia4

The compounds of the formula Ia5, in particular the compounds Ia5.1 to Ia5.285, which differ from the compounds Ia1.1 to Ia1.285 in that $R^{18}$ is ethyl and $R^{19}$ is methyl.

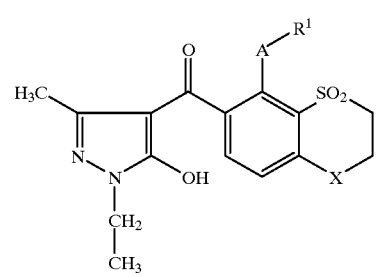

Ia5

The compounds of the formula Ia6, in particular the compounds Ia6.1 to Ia6.285, which differ from the compounds Ia1.1 to Ia1.285 in that $R^{18}$ is propyl and $R^{19}$ is methyl.

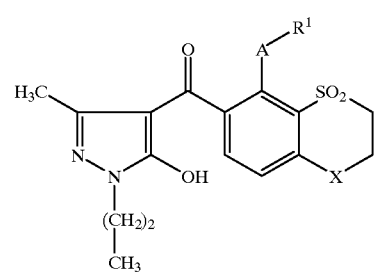

Ia6

The compounds of the formula Ia7, in particular the compounds Ia7.1 to Ia7.285, which differ from the compounds Ia1.1 to Ia1.285 in that $R^{17}$ is methylsulfonyloxy.

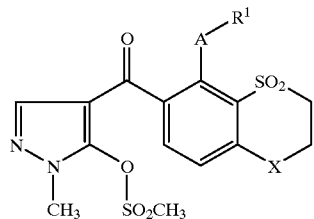
Ia7

The compounds of the formula Ia8, in particular the compounds Ia8.1 to Ia8.285, which differ from the compounds Ia1.1 to Ia1.285 in that R17 is methylsulfonyloxy and $R^{18}$ is ethyl.

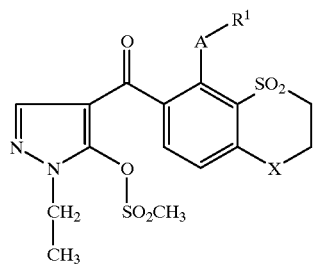
Ia8

The compounds of the formula Ia9, in particular the compounds Ia9.1 to Ia9.285, which differ from the compounds Ia1.1 to Ia1.285 in that $R^{17}$ is methylsulfonyloxy and $R^{18}$ is propyl.

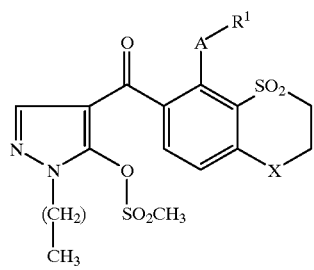
Ia9

The compounds of the formula Ia10, in particular the compounds Ia10.1 to Ia10.285, which differ from the compounds Ia1.1 to Ia1.285 in that $R^{17}$ is methylsulfonyloxy and $R^{19}$ is methyl.

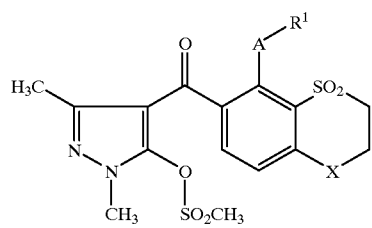
Ia10

The compounds of the formula Ia11, in particular the compounds Ia11.1 to Ia11.285, which differ from the compounds Ia1.1 to Ia1.285 in that $R^{17}$ is methylsulfonyloxy, $R^{18}$ is ethyl and $R^{19}$ is methyl.

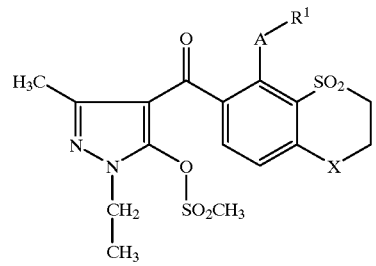
Ia11

The compounds of the formula Ia12, in particular the compounds Ia12.1 to Ia12.285, which differ from the compounds Ia1.1 to Ia1.285 in that $R^{17}$ is methylsulfonyloxy, $R^{18}$ is propyl and $R^{19}$ is methyl.

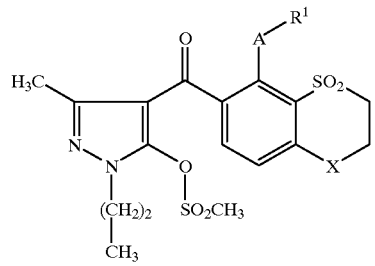
Ia12

The compounds of the formula Ia13, in particular the compounds Ia13.1 to Ia13.285, which differ from the compounds Ia1.1 to Ia1.285 in that $R^{17}$ is 4-methylphenylsulfonyloxy.

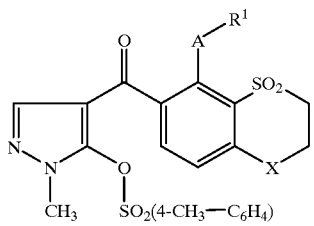
Ia13

The compounds of the formula Ia14, in particular the compounds Ia14.1 to Ia14.285, which differ from the compounds Ia1.1 to Ia1.285 in that $R^{17}$ is 4-methylphenylsulfonyloxy and $R^{18}$ is ethyl.

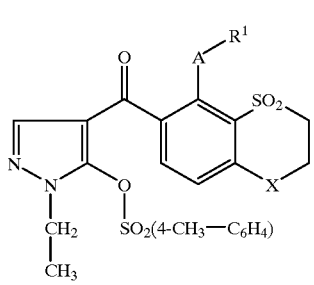
Ia14

The compounds of the formula Ia15, in particular the compounds Ia15.1 to Ia15.285, which differ from the compounds Ia1.1 to Ia1.285 in that $R^{17}$ is 4-methylphenylsulfonyloxy and $R^{18}$ is propyl.

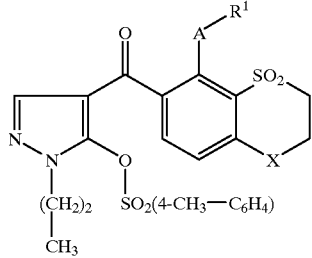

Ia15

The compounds of the formula Ia16, in particular the compounds Ia16.1 to Ia16.285, which differ from the compounds Ia1.1 to Ia1.285 in that $R^{17}$ is 4-methylphenylsulfonyloxy and $R^{19}$ is methyl.

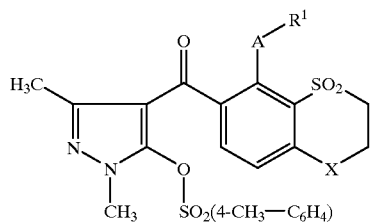

Ia16

The compounds of the formula Ia17, in particular the compounds Ia17.1 to Ia17.285, which differ from the compounds Ia1.1 to Ia1.285 in that $R^{17}$ is 4-methylphenylsulfonyloxy, $R^{18}$ is ethyl and $R^{19}$ is methyl.

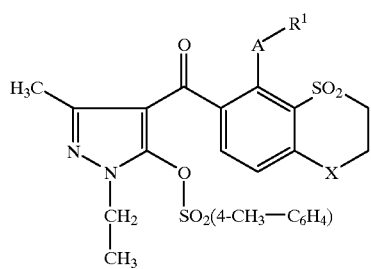

Ia17

The compounds of the formula Ia18, in particular the compounds Ia18.1 to Ia18.285, which differ from the compounds Ia1.1 to Ia1.285 in that $R^{17}$ is 4-methylphenylsulfonyloxy, $R^{18}$ is propyl and $R^{19}$ is methyl.

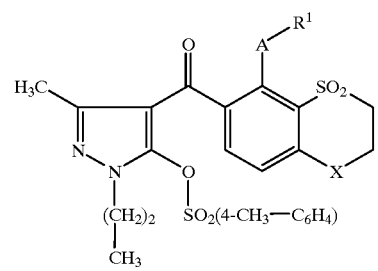

Ia18

The compounds of the formula Ia19, in particular the compounds Ia19.1 to Ia19.285, which differ from the compounds Ia1.1 to Ia1.285 in that $R^{17}$ is phenylcarbonylmethoxy.

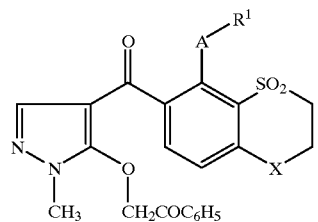

Ia19

The compounds of the formula Ia20, in particular the compounds Ia20.1 to Ia20.285, which differ from the compounds Ia1.1 to Ia1.285 in that $R^{17}$ is phenylcarbonylmethoxy and $R^{18}$ is ethyl.

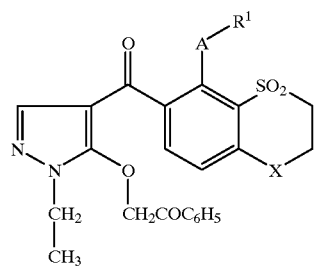

Ia20

The compounds of the formula Ia21, in particular the compounds Ia21.1 to Ia21.285, which differ from the compounds Ia1.1 to Ia1.285 in that $R^{17}$ is phenylcarbonylmethoxy and $R^{18}$ is propyl.

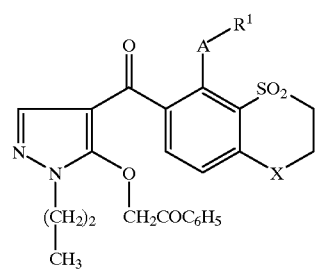

Ia21

The compounds of the formula Ia22, in particular the compounds Ia22.1 to Ia22.285, which differ from the compounds Ia1.1 to Ia1.285 in that $R^{17}$ is phenylcarbonylmethoxy and $R^{18}$ is methyl.

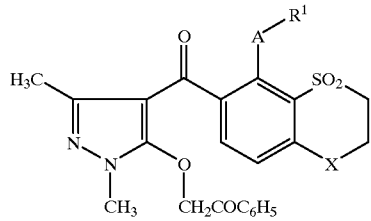

Ia22

The compounds of the formula Ia23, in particular the compounds Ia23.1 to Ia23.285, which differ from the compounds Ia1.1 to Ia1.285 in that $R^{17}$ is phenylcarbonylmethoxy, $R^{18}$ is ethyl and $R^{19}$ is methyl.

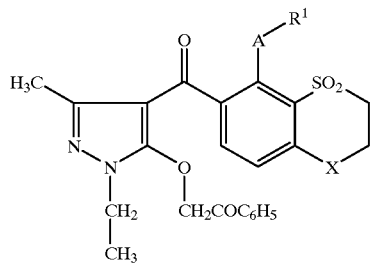

Ia23

The compounds of the formula Ia24, in particular the compounds Ia24.1 to Ia24.285, which differ from the compounds Ia1.1 to Ia1.285 in that $R^{17}$ is phenylcarbonylmethoxy, $R^{18}$ is propyl and $R^{19}$ is methyl.

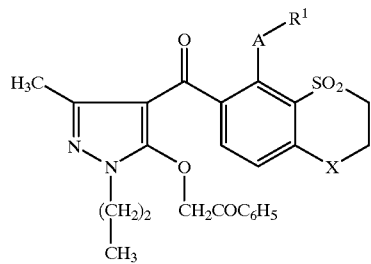

Ia24

The compounds of the formula Ia25, in particular the compounds Ia25.1 to Ia25.285, which differ from the compounds Ia1.1 to Ia1.285 in that $R^{17}$ is 4-methylphenylmethoxy.

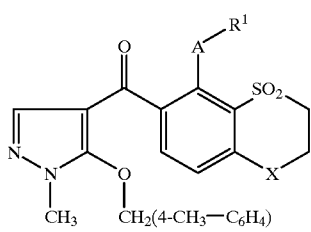

Ia25

The compounds of the formula Ia26, in particular the compounds Ia26.1 to Ia26.285, which differ from the compounds Ia1.1 to Ia1.285 in that $R^{17}$ is 4-methylphenylmethoxy and $R^{18}$ is ethyl.

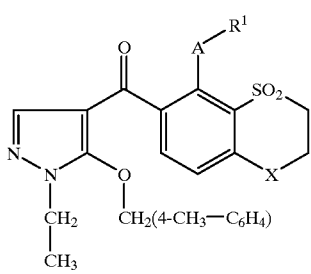

Ia26

The compounds of the formula Ia27, in particular the compounds Ia27.1 to Ia27.285, which differ from the compounds Ia1.1 to Ia1.285 in that $R^{17}$ is 4-methylphenylmethoxy and $R^{18}$ is propyl.

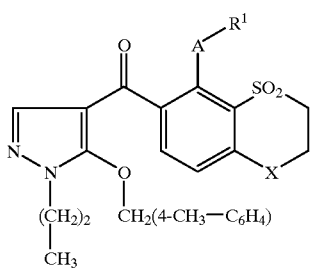

Ia27

The compounds of the formula Ia28, in particular the compounds Ia28.1 to Ia28.285, which differ from the compounds Ia1.1 to Ia1.285 in that $R^{17}$ is 4-methylphenylmethoxy and $R^{19}$ is methyl.

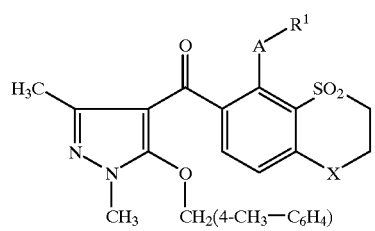

Ia28

The compounds of the formula Ia29, in particular the compounds Ia29.1 to Ia29.285, which differ from the compounds Ia1.1 to Ia1.285 in that $R^{17}$ is 4-methylphenylmethoxy, $R^{18}$ is ethyl and $R^{19}$ is methyl.

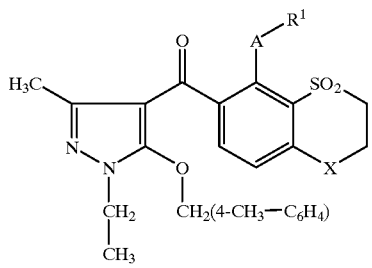

Ia29

The compounds of the formula Ia30, in particular the compounds Ia30.1 to Ia30.285, which differ from the compounds Ia1.1 to Ia1.285 in that $R^{17}$ is 4-methylphenylmethoxy, $R^{18}$ is propyl and $R^{19}$ is methyl.

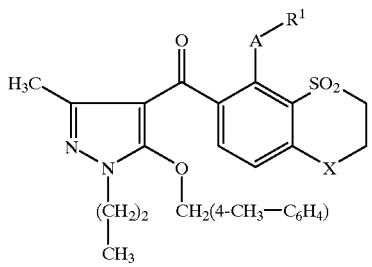

Ia30

The thiochromanoylpyrazolone derivatives of formula I can be obtained by various routes, for example by the following processes:

A. Preparation of compounds of the formula I where $R^{17}$=hydroxyl by reacting an activated carboxylic acid IVa or a carboxylic acid IVb, which is preferably activated in situ, with a pyrazolone of the formula III to give the acylation product, followed by rearrangement.

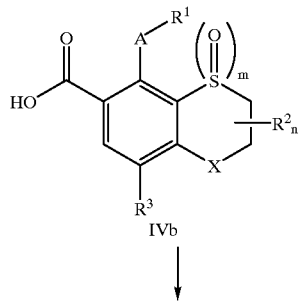

IVb

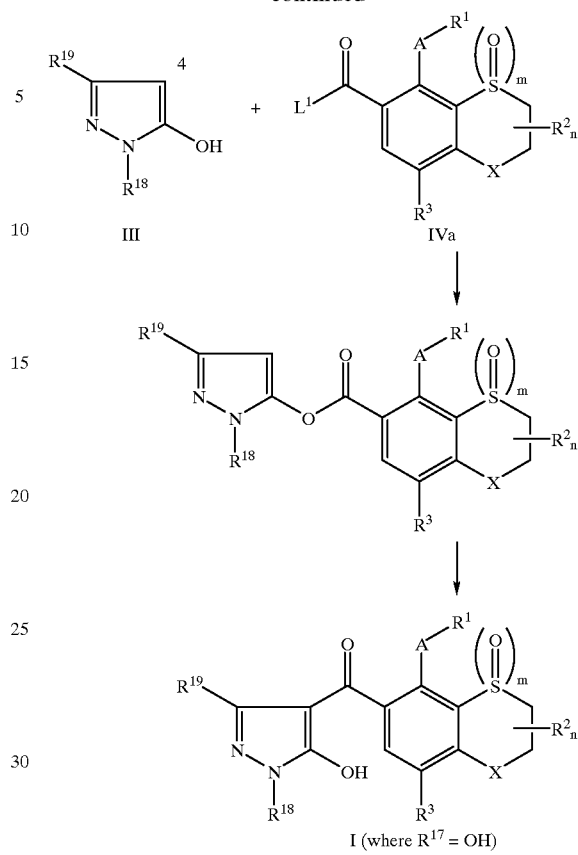

$L^1$ represents a nucleophilically replaceable leaving group, such as halogen, for example bromine or chlorine, hetaryl, for example imidazolyl or pyridyl, carboxylate, for example acetate or trifluoroacetate, etc.

The activated benzoic acid IVa can be employed directly, as in the case of the benzoyl halides, or generated in situ, for example using dicyclohexylcarbodiimide, triphenylphosphine/azodicarboxylic ester, 2-pyridine disulfide/triphenylphosphine, carbonyldiimidazole, etc.

If appropriate, it may be advantageous to carry out the acylation reaction in the presence of a base. Here, the reactants and the auxiliary base are expediently employed in equimolar amounts. A slight excess of auxiliary base, for example from 1.2 to 1.5 molar equivalents, based on IVa or IVb, may be advantageous in certain cases.

Suitable auxiliary bases are tertiary alkyl amines, pyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl-tert-butyl ether, tetrahydrofuran or dioxane, polar aprotic solvents, such as acetonitrile, dimethylformamide or dimethyl sulfoxide, or esters, such as ethyl acetate, or mixtures of these.

If the activated carboxylic acid component used is a benzoyl halide, it may be expedient to cool the reaction mixture to 0–10° C. during the addition of this reaction partner. The mixture is subsequently stirred at 20–100° C., preferably at 25–500° C., until the reaction is complete.

Work-up is carried out in a customary manner, for example by pouring the reaction mixture into water and extracting the product of value. Solvents which are suitable for this purpose are, in particular, methylene chloride, diethyl ether and ethyl acetate. After the organic phase has been dried and the solvent has been removed, the crude ester can be used for the rearrangement without any further purification.

The rearrangement of the esters to the compounds of the formula I is expediently carried out at 20–100° C. in a solvent and in the presence of a base and, if appropriate, using a cyano compound as catalyst.

Solvents which may be used are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in equimolar amounts or up to four-fold excess, based on the ester. Preference is given to using triethylamine or alkali metal carbonate, preferably in twice the equimolar ratio, based on the ester.

Suitable cyano compounds are inorganic cyanides, such as sodium cyanide or potassium cyanide, and organic cyano compounds, such as acetone cyanohydrin or trimethylsilyl cyanide. They are employed in an amount of from 1 to 50 mol percent, based on the ester. Preference is given to using acetone cyanohydrin or trimethylsilylcyanide, for example in an amount of from 5 to 15, preferably approximately 10, mol percent, based on the ester.

Work-up can be carried out in a manner known per se. The reaction mixture is acidified, for example with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the precipitate which forms is filtered off with suction, and/or extracted with methylene chloride or ethyl acetate, dried and concentrated.

B. Preparation of compounds of the formula I where $R^{17}$=halogen by reacting thiochromanoylpyrazolone derivatives of the formula I (where $R^{17}$=hydroxyl) with halogenating agents:

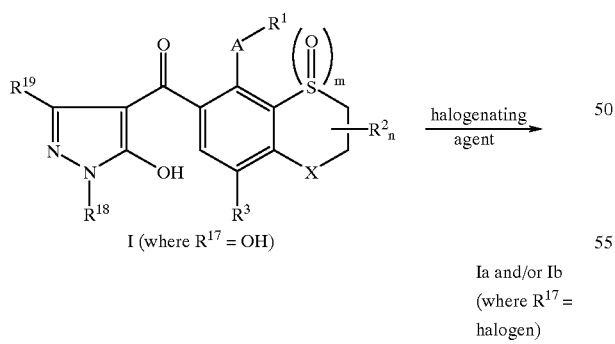

Suitable halogenating agents are, for example, phosgene, diphosgene, triphosgene, thionylchloride, oxalylchloride, phosphorus oxychloride, phosphorus pentachloride, mesyl chloride, chloromethylene-N,N-dimethylammonium chloride, oxalyl bromide, phosphorus oxybromide, etc.

C. Preparation of compounds of the formula I where $R^{17}$=$OR^{20}$, $OSO_2R^{21}$, $OPOR^{22}R^{23}$ or $OPSR^{22}R^{23}$ by reacting thiochromanoylpyrazolone derivatives of the formula I (where $R^{17}$=hydroxyl) with alkylating, sulfonylating or phosphonylating agents Vα, Vβ, Vγ or Vδ.

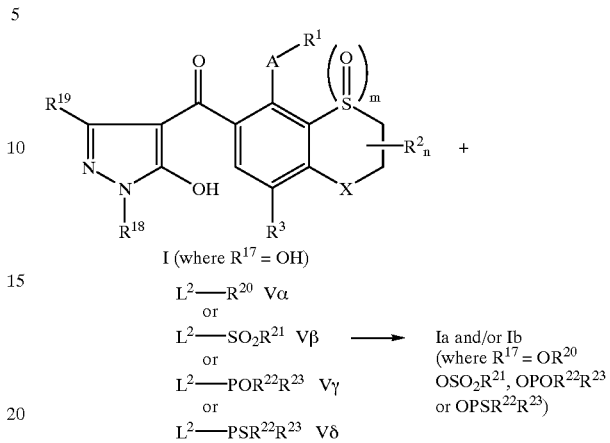

$L^2$ is a nucleophilically replaceable leaving group, such as halogen, for example chlorine or bromine, hetaryl, for example imidazolyl, carboxylate, for example acetate, or sulfonate, for example mesylate or triflate, etc.

The compounds of the formula Vα, Vβ, Vγ or Vδ can be employed directly, such as, for example, in the case of the carbonyl halides, or generated in situ, for example activated carboxylic acids (with carboxylic acid and dicyclohexylcarbodiimide, etc.).

D. Preparation of compounds of the formula I where $R^{17}$=$OR^{20}$, $SR^{20}$, $POR^{22}R^{23}$, $NR^{24}R^{25}$, $ONR^{21}R^{21}$ or N-bonded heterocyclyl by reacting compounds of the formula I where $R^{17}$=halogen, $OSO_2R^{21}$ with compounds of the formula VIα, VIβ, VIγ, VIδ, VIε or VIη, if appropriate in the presence of a base or with previous salt formation.

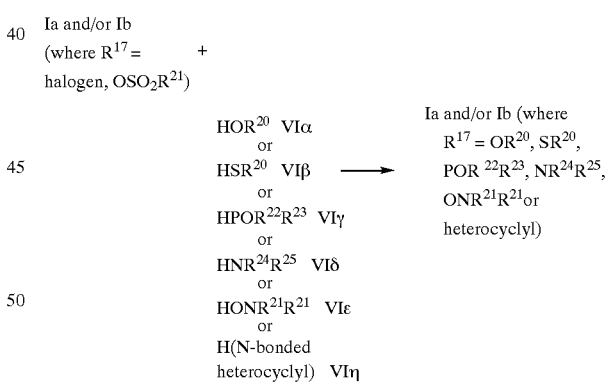

E. Preparation of compounds of the formula I where $R^{17}$=$SOR^{21}$, $SO_2R^{21}$ by reacting compounds of the formula I where $R^{17}$=$SR^{21}$ with an oxidizing agent.

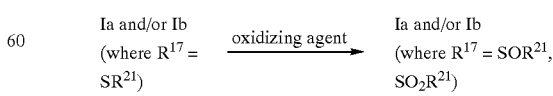

Suitable oxidizing agents are, for example, m-chloroperbenzoic acid, peroxy acetic acid, trifluoroperoxyacetic acid, hydrogen peroxide, if appropriate in the presence of a catalyst, such as tungstate.

For the reactions mentioned under points B to E, the following conditions apply:

The starting materials are usually employed in equimolar ratios. However, it may also be advantageous to use an excess of one component or the other.

If appropriate, it may be advantageous to carry out the reactions in the presence of a base. Here, the reactants and the base are expediently employed in equimolar amounts.

With respect to the processes C and D, it may, in certain cases, be advantageous to employ an excess of base, for example from 1.5 to 3 molar equivalents, in each case based on the starting material.

Suitable bases are tertiary alkyl amines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example, toluene, xylene or chlorobenzene, ethers, such as diethyl ether, methyl-tert-butyl ether, tetrahydrofuran or dioxane, polar aprotic solvents, such as acetonitrile, dimethylformamide or dimethylsulfoxide, or esters, such as ethyl acetate, or mixtures of these.

The reaction temperature is usually in the range from 0° C. to the boiling point of the reaction mixture.

Work-up can be carried out in a manner known per se to give the product.

Depending on the reaction conditions, in the processes B to D the compounds Ia, Ib or mixtures of these may be formed. The latter can be separated by classic separation methods, such as, for example, crystallization, chromatography, etc.

F. Preparation of compounds of the formula I where $R^{16}$=IIa by reacting a metallated pyrazole derivative of the formula VII with a carboxylic acid derivative of the formula IVa:

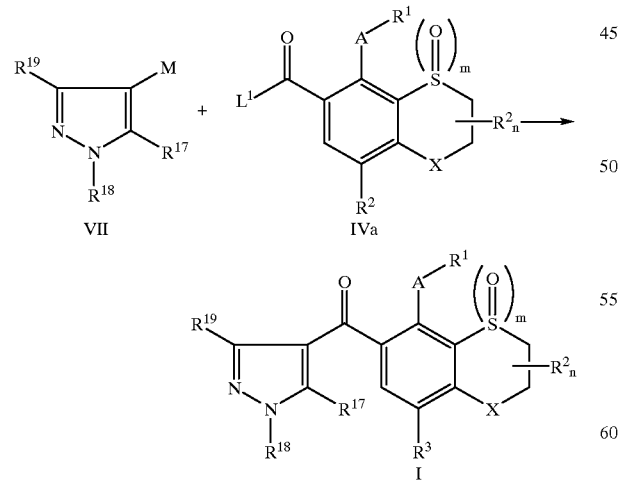

Here, M is a metal, in particular an alkali metal, such as lithium or sodium, an alkaline earth metal, such as, for example, magnesium, or a transition metal, such as palladium, nickel, etc. and $L^1$ is a nucleophilically replaceable leaving group such as halogen, for example chlorine or bromine, alkylsulfonate, such as mesylate, haloalkylsulfonate, such as triflate or cyanide.

The reaction is usually carried out at from $-100°$ C. to the reflux temperature of the reaction mixture. Suitable solvents are inert aprotic solvents, such as ethers, for example diethyl ether, tetrahydrofuran. The compounds of the formula IVa are usually employed in excess, but it may also be advantageous to employ them in equimolar amounts or in substoichiometric amounts. Work-up is carried out to give the product.

The metallated pyrazole derivatives of the formula VII can be formed in a manner known per se by reacting pyrazoles which are halogenated in 4-position with metals such as lithium, sodium, magnesium, etc., or with organometallic compounds, such as, for example, butyllithium. However, it is also possible to metallate pyrazoles which are linked to hydrogen in the 4-position directly, for example using the abovementioned metals or organometallic compounds. The reactions are usually carried out in an inert aprotic solvent, preferably in ethers, such as diethyl ether, tetrahydrofuran, etc. The reaction temperature is in the range from $-100°$ C. to the boiling point of the reaction mixture. The compounds of the formula VII are usually directly reacted further or generated in situ.

The pyrazolones of the formula III used as starting materials are known or can be prepared by processes known per se (for example EP-A 240 001, J. Chem. Soc. 315, 383 (1997)).

The alkylating agents Vα, sulfonylating agents Vβ, phosphonylating agents Vγ or Vδ, and the compounds VIα, VIβ, VIγ, VIδ and VIε are likewise known, or they can be prepared analogously to known processes.

The carboxylic acid derivatives of the formula IV

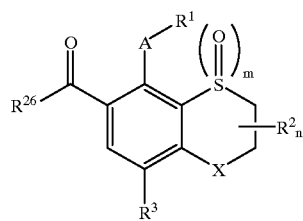

where:

A is $C_1$–$C_6$-alkandiyl, $C_2$–$C_6$-alkenediyl, $C_4$–$C_6$-alkanedienediyl or $C_2$–$C_6$-alkynediyl, where the abovementioned radicals may carry one or two substituents from the following group: cyano, $C_1$–$C_4$-alkoxy, $C_1$–$C_4$-alkylthio, $C_1$–$C_4$-alkylcarbonyl or $C_1$–$C_4$-alkoxycarbonyl;

$R^1$ is cyano, thiocyanato, nitro, $OR^4$, $SR^5$, $SOR^6$, $SO_2R^6$, $ONR^6R^7$, ON=$CR^6R^8$, $NR^9R^{10}$, $P(O)R^{11}R^{12}$, $P(S)R^{11}R^{12}$, $COR^6$, $CO_2R^6$, phenyl, heterocyclyl or N-bonded heterocyclyl, where the three last-mentioned radicals for their part may be partially or fully halogenated and/or may carry one to three substituents from the following group: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^2$ is $C_1$–$C_6$-alkyl, $C_1$–$C_6$-haloalkyl, $C_1$–$C_6$-alkoxy or $C_1$–$C_6$-haloalkoxy;

$R^3$ is hydrogen, halogen or $C_1$–$C_6$-alkyl;

X is oxygen, sulfur, S=O, S(=O)$_2$, $CR^{13}R^{14}$, C=O or C=$NR^{15}$;

m is 0, 1 or 2;

n is 0, 1, 2, 3 or 4;

$R^4$, $R^5$ are one of the radicals mentioned under $R^6$;
are hydrogen, $C_1$–$C_4$-alkylcarbonyl, $C_1$–$C_4$-haloalkylcarbonyl, $C_1$–$C_4$-alkoxycarbonyl, $C_1$–$C_4$-haloalkoxycarbonyl, $C_1$–$C_4$-alkylsulfonyl, $C_1$–$C_4$-haloalkylsulfonyl, $P(O)R^{11}R^{12}$ or $P(S)R^{11}R^{12}$;
are phenylcarbonyl, phenoxycarbonyl, phenyl-$C_1$–$C_4$-alkylcarbonyl, phenylsulfonyl, phenoxysulfonyl, heterocyclylcarbonyl, heterocyclyloxycarbonyl, heterocyclyl-$C_1$–$C_4$-alkylcarbonyl, heterocyclylsulfonyl or heterocyclyloxysulfonyl, where the phenyl and the heterocyclyl radical of the ten last mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^6$ is $C_1$–$C_6$-alkyl, $C_3$–$C_6$-alkenyl, $C_3$–$C_6$-alkinyl or $C_3$–$C_6$-cycloalkyl, where the four above mentioned radicals may be partially or fully halogenated and/or may carry one to three of the following groups:
cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl, $C_1$–$C_4$-alkylcarbonyl, $C_1$–$C_4$-alkoxycarbonyl and $C_1$–$C_4$-haloalkoxycarbonyl;
is phenyl, phenyl-$C_1$–$C_4$-alkyl, heterocyclyl or heterocyclyl-$C_1$–$C_4$-alkyl, where the phenyl and the heterocyclyl radical of the four last mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^7$ is hydrogen or $C_1$–$C_6$-alkyl;

$R^8$ is hydrogen, $C_1$–$C_6$-alkyl, $C_1$–$C_6$-alkoxycarbonyl, cyano or $C_1$–$C_6$-alkoxy;

$R^9$ is one of the radicals mentioned under $R^4$;
is $C_1$–$C_6$-alkoxy, $C_3$–$C_6$-alkenyloxy, $C_3$–$C_6$-alkinyloxy, aminocarbonyl, N—$C_1$–$C_6$-alkylaminocarbonyl or N,N-di-($C_1$–$C_6$-alkyl)aminocarbonyl;

$R^{10}$ is hydrogen, $C_1$–$C_6$-alkyl, $C_3$–$C_6$-alkenyl or $C_3$–$C_6$-alkinyl;

$R^{11}$, $R^{12}$ are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{13}$, $R^{14}$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, N—$C_1$–$C_6$-alkylamino, N—$C_1$–$C_6$-haloalkylamino, N,N—(di-$C_1$–$C_6$-alkyl)amino, N—$C_1$–$C_6$-alkoxyamino, N—($C_1$–$C_6$-alkoxy)—N—($C_1$–$C_6$-alkyl)amino, 1-tetrahydropyrrolyl, 1-piperidinyl, 4-morpholinyl or 1-hexahydropyrazinyl;
or
$R^{13}$, $R^{14}$ together form a methylidene group which may be substituted by one or two substituents from the following group: halogen, cyano, $C_1$–$C_6$-alkyl, $C_1$–$C_6$-haloalkyl, $C_1$–$C_6$-alkoxy or $C_1$–$C_6$-haloalkoxy;

$R^{15}$ is $C_1$–$C_6$-alkyl, $C_1$–$C_6$-haloalkyl, $C_1$–$C_6$-alkoxy or $C_1$–$C_6$-haloalkoxy;

$R^{26}$ is hydroxyl or a radical which can be removed by hydrolysis;

are novel.

Examples of radicals which can be removed by hydrolysis are alkoxy, phenoxy, alkylthio and phenylthio radicals which may be unsubstituted or substituted, halides, hetaryl radicals which are attached via nitrogen, amino and imino radicals which may be unsubstituted or substituted, etc.

Preference is given to carbonyl halides of the formula IVa where $R^{26}$=halogen

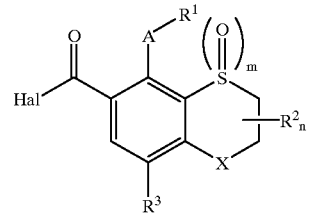

IVa where the variables A, X, $R^1$ to $R^3$, m and n are as defined under formula IV and Hal is halogen, in particular chloride or bromide.

Likewise, preference is given to carboxylic acids of the formula IVb

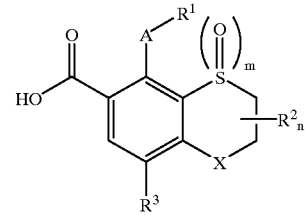

IVb where the variables A, X, $R^1$ to $R^3$, m and n are as defined under formula IV.

Likewise, preference is given to carboxylic esters of the formula IVc

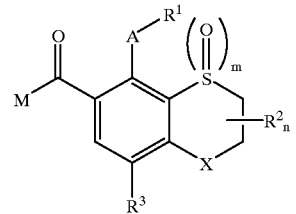

IVc where the variables A, X, $R^1$ to $R^3$, m and n are as defined under formula IV and M is $C_1$–$C_6$-alkoxy.

The particularly preferred embodiments of the carboxylic acid derivatives of the formula IV with respect to the variables A, X, $R^1$ to $R^3$, m and n correspond to those of the thiochromanoylpyrazolone derivatives of the formula I.

The carbonyl halides of the formula IVa (IV where $R^{26}$=Hal, in particular Cl, Br) can be prepared in a manner known per se (cf. L. G. Fieser, M. Fieser "Reagents for Organic Synthesis", Vol. I, pp. 767–769 (1967)) by reacting the carboxylic acids of the formula IVb with halogenating reagents, such as thionyl chloride, thionyl bromide, phosgene, diphosgene, triphosgene, oxalyl chloride or oxalyl bromide.

The benzoic acids of the formula IVb can be prepared in a known manner by acidic or basic hydrolysis from the corresponding carboxylic esters IVc (IV where M=$C_1$–$C_6$-alkoxy) (J. March, "Advanced Organic Chemistry", 4th Edition, p. 378 ff., Wiley-Interscience Publication, 1992).

The carboxylic esters of the formula IVc are obtainable by various routes, for example by one of the following processes:

1. Preparation of compounds of the formula IVc, especially where A=$C_1$–$C_6$-alkandiyl, in particular methanediyl, by reacting compounds of the formula VIII, where $L^3$ is a nucleophilically replaceable leaving group, such as halogen, for example chlorine or bromine, alkylsulfonate, for example mesylate, haloalkylsulfonate, for example triflate, or cyanide,

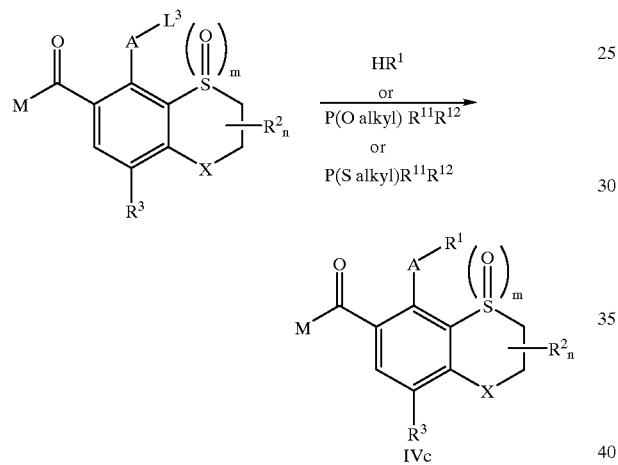

with suitable nucleophiles $HR^1$ or phosphites, for example according to Arbuzow (J. March, "Advanced Organic Chemistry", 4th Edition, p. 959, Wiley-Interscience Publication, 1992).

2. Preparation of compounds of the formula IVc where $R^1$=$SOR^6$ or $SO_2R^6$ by reacting compounds of the formula IVc where $R^1$=$SR^6$ with an oxidizing agent.

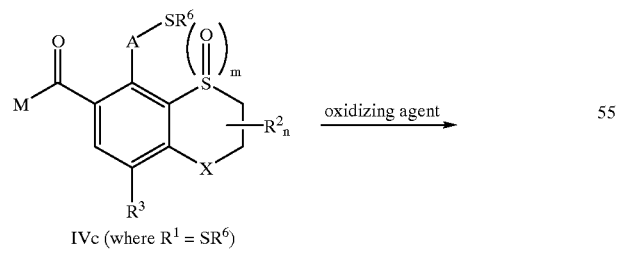

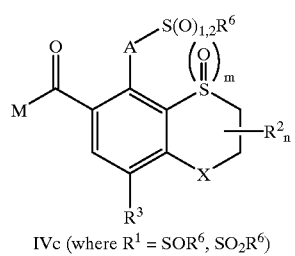

Suitable oxidizing agents are, for example, m-chloroperbenzoic acid, peroxyacetic acid, trifluoroperoxyacetic acid, hydrogen peroxide, if appropriate in the presence of a catalyst, such as tungstate.

3. Preparation of compounds of the formula IVc where $R^1$=$P(S)R^{11}R^{12}$ by reacting compounds of the formula IVc where $R^1$=$P(O)R^{11}R^{12}$ with sulfurizing agents, such as $P_4S_{10}$ (cf. I. W. Still et al., Can. J. Chem. 56, 1423 (1978)), Lawessons Reagent (cf. A. Shabana et al., Chem. Ind. (London) 15, 553 (1984)) or p-toluene disulfide (cf. K. Takuyuki et al., Chem. Lett. 501 (1986)).

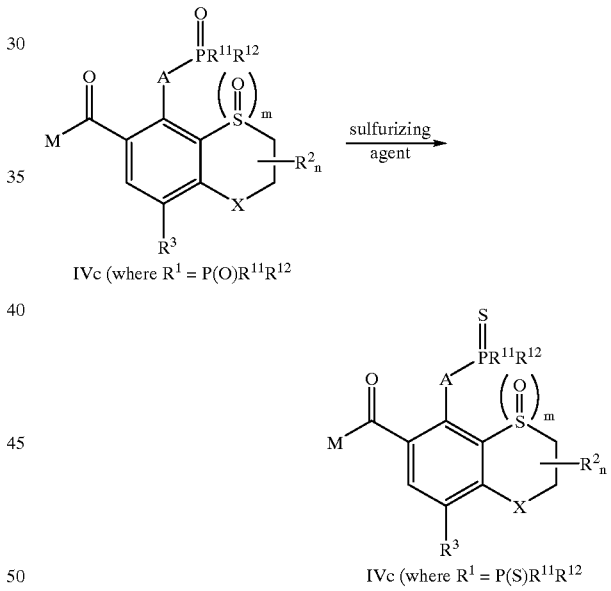

4. Preparation of compounds of the formula IVc where A=$C_2$–$C_6$-alkandiyl, $C_3$–$C_6$-alkendiyl, $C_3$–$C_6$-alkynediyl, where the multiple bond is not conjugated to the phenyl ring, by reacting compounds of the formula VIII, where $L_3$ is a nucleophilically replaceable leaving group, such as halogen, for example chlorine or bromine, alkylsulfonate, for example mesylate or haloalkylsulfonate, for example triflate,

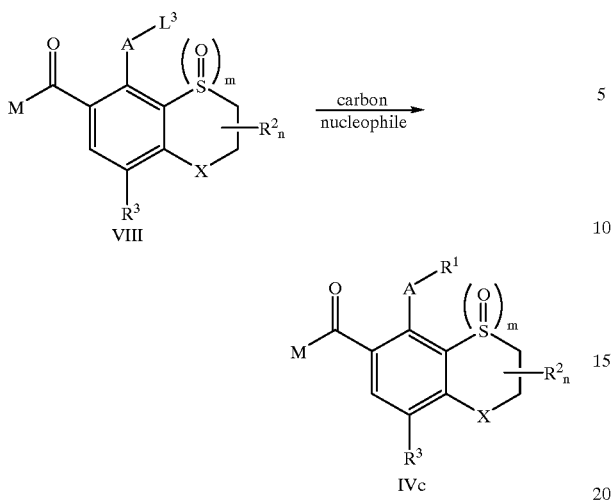

VIII

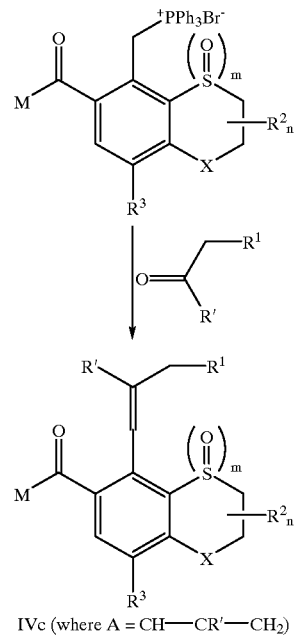

IVc with a carbon nucleophile. Suitable for this purpose are, for example organometallic, such as Grignard, organolithium or organo zinc compounds, or CH-acidic compounds such as aldehydes, ketones, carboxylic acid derivatives (esters, amides, etc.), nitriles, sulfones, 1,3-dithio compounds, diketones, dicarboxylic ester derivatives, ketocarboxylic acid derivatives, dinitriles, ketonitriles, cyanocarboxylic acid derivatives or bisulfones.

If appropriate, it may be advantageous in the reaction with CH-acidic compounds to employ bases, such as alkali metal or alkaline earth metal hydroxides, for example sodium hydroxide or potassium hydroxide, alkali metal or alkaline earth metal carbonates, for example sodium carbonate or potassium carbonate, alkali metal or alkaline earth metal bicarbonates, for example sodium bicarbonate or potassium bicarbonate, alkali metal or alkaline earth metal alkoxides, for example sodium methoxide, sodium ethoxide or potassium tert-butoxide, alkali metal or alkaline earth metal hydrides, for example sodium hydride, or organometallic bases, such as butyllithium.

5. Preparation of compounds of the formula IVc where $A=C_2-C_6$-alkendiyl, in particular where $A=C_2-C_6$-alkendiyl, where the double bond is conjugated to the phenyl ring, by reacting compounds of the formula VIII where $L^3$=halogen, in particular bromine, with triarylphosphines, such as triphenylphosphine, and subsequent reaction with appropriately substituted aldehydes or ketones in the presence of bases according to Wittig. Also suitable are related reactions, for example using phosphonates according to Horner-Emmons (cf. J. March, "Advanced Organic Chemistry, 4th Edition, p. 959 ff., Wiley-Interscience Publication, 1992).

By way of example, a Wittig reaction is shown below:

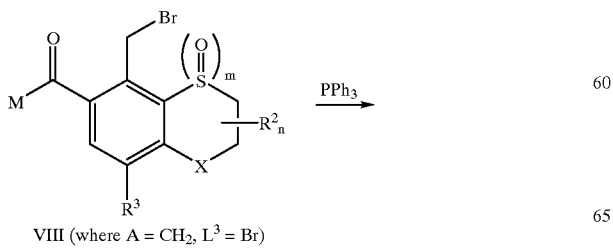

VIII (where $A = CH_2$, $L^3 = Br$)

Furthermore, these products can be obtained by using the "inverse starting materials", such as, for example

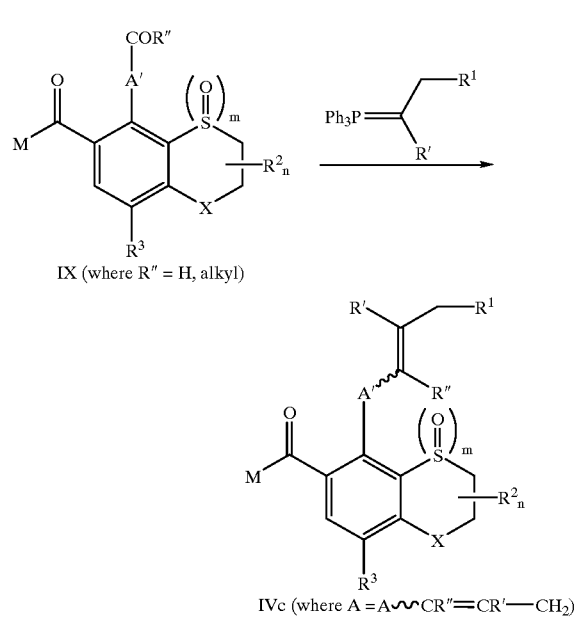

IX (where $R'' = H$, alkyl)

6. Preparation of compounds of the formula IVc where $A=C_2-C_6$-alkendiyl, in particular where $A=C_2-C_6$-alkendiyl, where the double bond is conjugated to the phenyl radical, by aldol reaction and related reactions in a manner known per se (cf. J. March, "Advanced Organic Chemistry", 4th edition, p. 937, Wiley-Interscience Publication, 1992)

7. Preparation of compounds of the formula IVc where $A=C_2-C_6$-alkynediyl, in particular where $A=C_2-C_6$-alkindiyl, where the triple bond is conjugated to the phenyl ring, by dehalogenating compounds of the formula X using a base, such as alkali metal or alkaline earth metal hydroxides, for example potassium hydroxide, analogously to processes known from the literature (cf. L. I. Smith et al., Org. Synth. 22, 50 (1942); E. V. Dehmlow et al., Liebigs Ann. Chem. 1 (1980).)

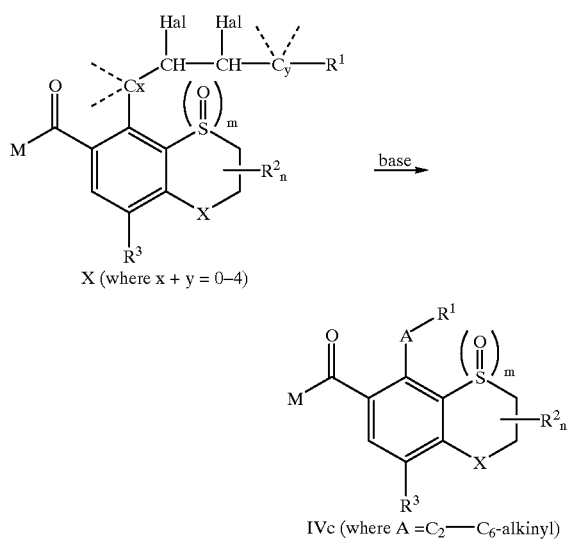

X (where x + y = 0–4)

IVc (where A =$C_2$—$C_6$-alkinyl)

The halide of the formula VIII, in particular where A=methanediyl, and $L^3$=bromine, can be obtained by halogenating the corresponding alkyl compounds XI in the presence of a free radical initiator or by irradiation.

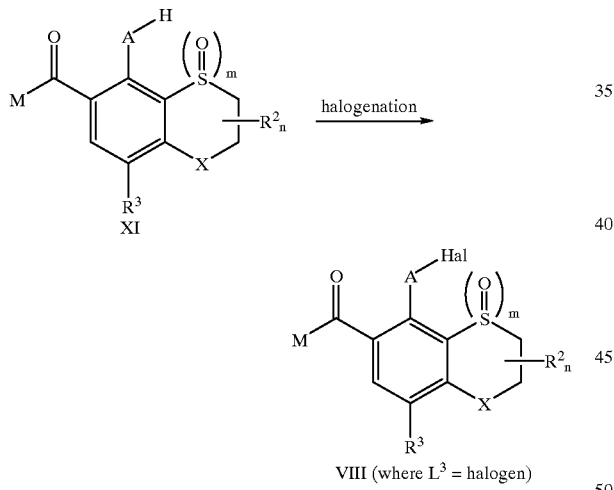

VIII (where $L^3$ = halogen)

Suitable halogenating agents are, for example, chlorine, bromine, N-chloroamine, N-N-chlorosuccinimide, N-bromosuccinimide etc. Suitable free radical initiators are, inter alia, benzoylperoxide or azobisisobutyronitrile. However, it is also possible to carry out the reaction under irradiation with suitable radiation sources, such as UV-Hg low-pressure or Hg high-pressure lamps.

Furthermore, the halides of the formula VIII, in particular where A=methanediyl and $L^3$=bromine, can be obtained by halogenating the corresponding alcohols XII.

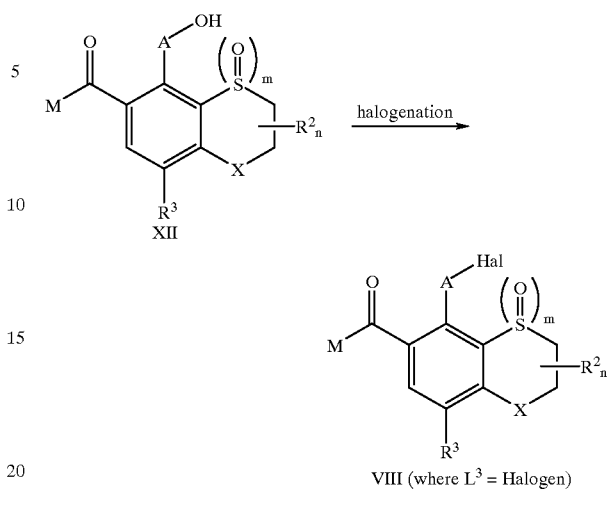

VIII (where $L^3$ = Halogen)

Suitable halogenating agents are phosphorus pentachloride, phosphorus oxychloride, phosphorus oxybromide, thionyl chloride, thionyl bromide, phosgene, carbonyl bromide, oxalyl chloride, oxalyl bromide, and binary systems, such as carbon tetrachloride/triphenylphosphine or carbon tetrabromide/triphenylphosphine, etc.

The alkyl sulfonates or haloalkyl sulfonates of the formula VIII, in particular where A=methanediyl, are obtainable by reacting alcohols of the formula XII with activated alkyl- or haloalkylsulfonic acids, such as alkyl- or haloalkylsulfonic anhydrides or alkyl- or haloalkylsulfonic halides.

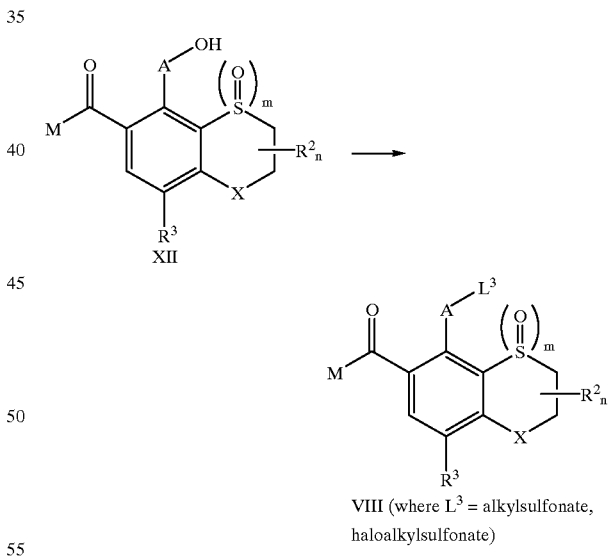

VIII (where $L^3$ = alkylsulfonate, haloalkylsulfonate)

The aldehydes or ketones of the formula IX, in particular where A'=bond can be obtained by oxidizing appropriate compounds of the formlua XII in a manner known per se.

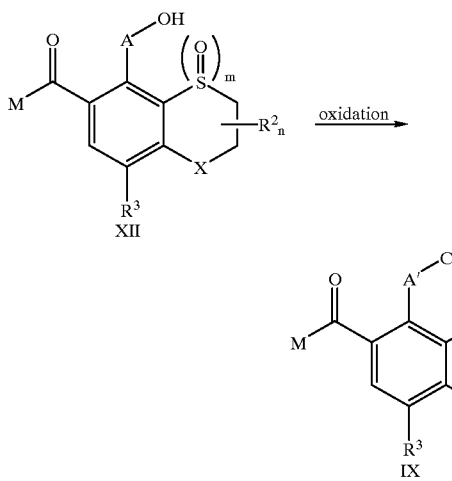

XII

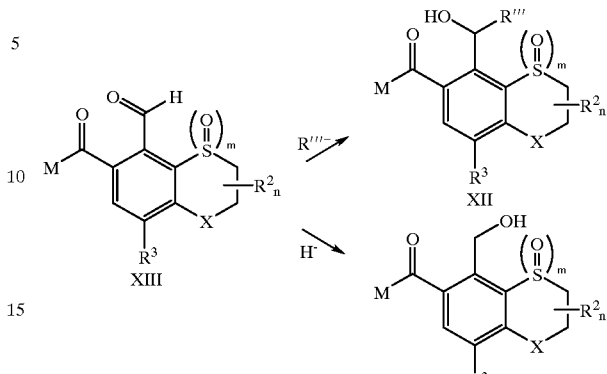

XII

Suitable oxidizing agents are, inter alia, hydrogen peroxide, chromic acid, potassium permanganate, pryidinium dichromate, cerium ammonium nitrate, N-methylmorpholine N-oxide or tetramethylmorpholine N-oxide) cf. J. March, "Advanced Organic Chemistry", 4th Edition, p. 1158 ff., Wiley-Interscience Publication, 1992).

The compounds of the formula X are prepared by halogenating the double bond of the compounds of the formula IVc where $A=C_2-C_6$-alkendiyl, analogously to processes known from the literature (cf. J. March, "Advanced Organic Chemistry", 4th Edition, p. 812 ff., Wiley-Interscience Publication, 1992).

The aldehyde of the formula XIII is obtainable by oxidizing compounds of the formula VIII where A=methanediyl and $L^3$=chlorine, bromine, in particular bromine.

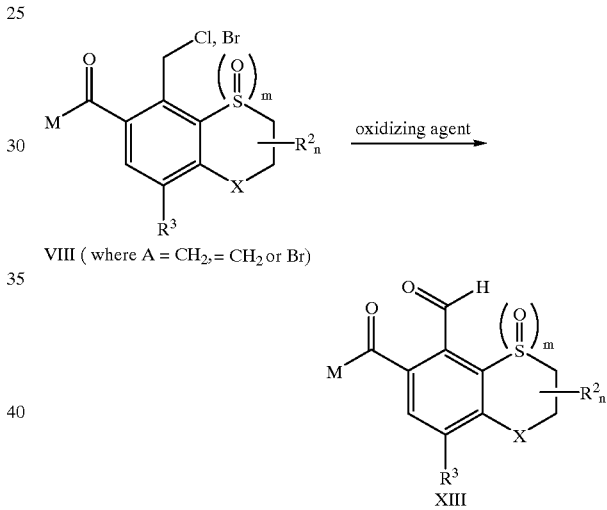

VIII (where A = $CH_2$, = $CH_2$ or Br)

XIII

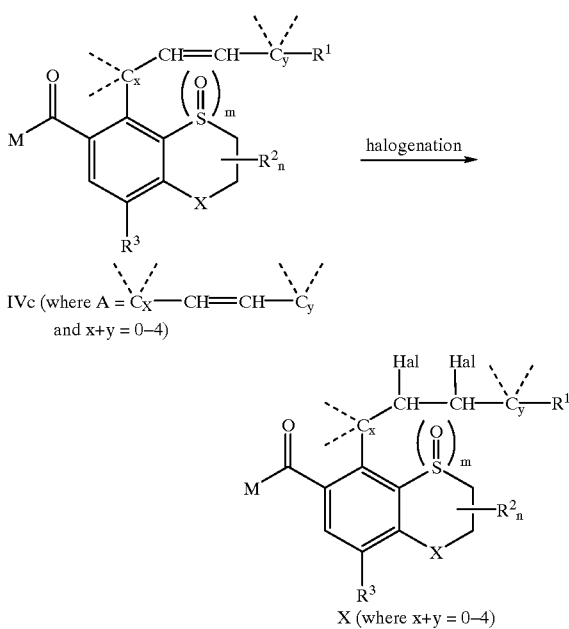

IVc (where A = $C_x$—CH=CH—$C_y$ and x+y = 0–4)

X (where x+y = 0–4)

Suitable halogenating agents are, in particular, chlorine or bromine.

The alcohols of the formula XII can be obtained in a manner known per se by reacting appropriate aldehydes or ketones with carbon nucleophiles. Suitable carbon nucleophiles are, for example, organometallic reagents, such as Grignard reagents, organolithium or organotin compounds, but also hydrides (or reducing agents such as lithium aluminum hydride, boranate, etc. or "hydride generating systems", such as reduction using hydrogen over a catalyst). This is described below by way of example.

Suitable oxidizing agents are, inter alia, barium permanganate ($Ba(MnO_4)_2$; cf. H. Firouzabadi et al., Tetrahedron 46, 6869 (1990)), silver nitrate ($AgNO_3$; cf. E. Ghera et al., Synthesis 504 (1984)), potassium dichromate ($K_2Cr_2O_7$; cf. E. Santaniello, Tetrahedron Lett. 4581 (1979)), bis-(p-methoxyphenyl)selenium oxide (cf. K. Ariyoshi et al., Chem. Lett. 6, 891 (1984)) or isopropyl nitrite (cf. S. Kuriatkowski et al., Tetrahedron Lett. 2093 (1990)).

If appropriate, it may be advantageous in the synthesis variants described above to introduce protective groups for certain functionalities if the functionalities are not compatible with the reaction conditions required. The choice of protective groups depends both on the reaction conditions and on the molecular structure. Protective groups, their introduction and removal are generally known from the literature (cf. T. W. Greene et al., "Protective Groups in Organic Synthesis", $2^{nd}$ Ed., Wiley-New York, 1991) and can be used analogously to processes known from the literature.

Furthermore, it may be necessary to carry out a combination of the synthesis variants described above.

Likewise, it is possible to introduce further substituents or to modify substituents that are already present, by electrophilic, nucleophilic, free-radical or organometallic reactions and also by oxidation or reduction reactions.

The reactions above are usually carried out at atmospheric pressure.

The reaction temperatures are generally between −100° C. and the reflux temperature of the reaction mixture.

In general, solvents or solvent mixtures are used which are suitable for the reaction conditions.

The starting materials are usually employed in stoichiometric amounts. However, it may also be advantageous to use less or more than the stoichiometric amount of one reactant or the other.

Furthermore, the synthesis of compounds of the formula XI (where X=S; m=0) below is novel:

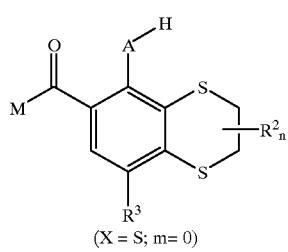

(X = S; m= 0)

In the literature, the synthesis of 5-methyl-2,3-dihydro-1,4-benzodithiine from the cyclic thioketal of 2-methyl-cyclohexanone using N-bromosuccinimide is described. However, the yield is below 50% (H. Tani et al., Heterocycles 36, 1783 (1993)).

It has now been found that the reaction of dithioketals of the formula XIV with a halogenating agent and subsequent treatment with a reducing agent gives satisfactory yields.

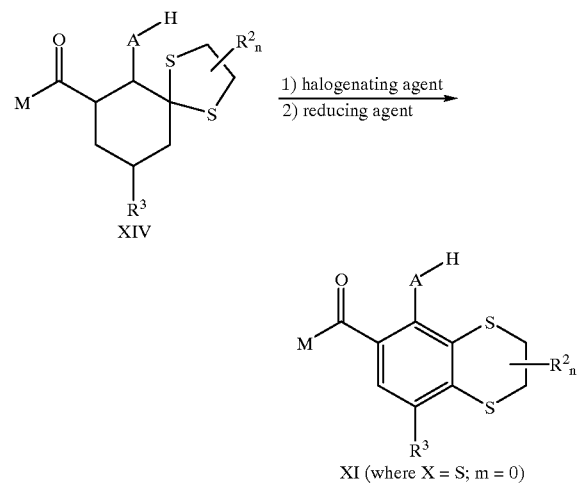

XI (where X = S; m = 0)

Suitable halogenating agents are, inter alia, N-bromosuccinimide, N-chlorosuccinimide, bromine or chlorine. They are generally employed in a three-fold excess, based on the starting materials. However, it may also be advantageous to employ a greater or smaller excess. Suitable solvents for the first step of this synthesis are, inter alia, inert solvents, such as halogenated hydrocarbons, for example dichloromethane, trichloromethane, carbon tetrachloride, 1,2-dichloroethane, chlorobenzene, etc. or aromatics, such as benzene, toluene or xylene. It may also be advantageous to use solvent mixtures. The reaction temperatures during the first step are generally from −80° C. to the reflux temperature of the reaction mixture. The reaction is preferably carried out at from −80° C. to room temperature, in particular at from −80° C. to 0° C.

Suitable reducing agents are alanates, such as lithium alanate, diisobutylaluminum hydride, boranates, such as sodium boranate, diborane, metal hydrides, such as trialkyltin hydride, metals, such as zinc, tin, etc. The reducing agent is generally employed in equimolar amounts. However, it may also be advantageous to use more or less than the stoichiometric amount. Suitable solvents for the second reaction step are, in particular, inert solvents, such as ethers, for example diethyl ether, methyl tert-butyl ether or 1,4-dioxane, or dipolar solvents, such as dimethylformamide, diethylformamide, dimethyl sulfoxide, N-methyl pyrrolidone. However, it is also possible to use alcohols, such as methanol, ethanol, etc. The reaction is generally carried out at from 0° C. to the reflux temperature of the reaction mixture, preferably at from 0 to 100° C., in particular at from 10 to 40° C.

The preparation of the compounds of the formula XIV from the corresponding cyclohexanone derivatives is carried out by reaction with dithiols, using methods known per se (Cf. T. W. Greene, et al. in "Protective Groups in Organic Synthesis", 2nd Edition, pp. 201–203, Wiley, New York, 1991).

PREPARATION EXAMPLES 1. 4-{[4,4-Dimethyl-8-propoxymethyl-1,1-dioxothiochroman-7-yl]-carbonyl}-5-hydroxy-1-methylpyrazole (Compound 2.17)

Step a) Methyl 3-(3-methyl-2-butenylthio)-2-methylbenzoate 43.5 g (0.275 mol) of 3-methyl-2-butenyl bromide were added dropwise to 50 g (0.275 mol) of methyl 3-thio-2-methyl-benzoate, and 37.9 g (0.275 mol) of potassium carbonate in 250 ml of acetone, and the mixture was stirred at room temperature overnight. The solvent was removed, the residue was taken up in water/ethyl acetate and the organic phase was dried and concentrated to dryness.

Yield: 67.9 g (99%); $^1$H-NMR (CDCl$_3$): δ (in ppm)=7.63 (d, 1H); 7.41 (d, 1H); 7.16 (t, 1H); 5.25 (m, 1H); 3.90 (s, 3H); 3.49 (d, 2H); 2.60 (s, 3H); 1.70 (s, 3H); 1.56 (s, 3H).

Step b) Methyl 4,4,8-trimethylthiochromane-7-carboxylate

At −5 to 0° C., 206.4 g (1.09 mol) of titanium tetrachloride in 600 ml of methylene chloride were added dropwise to 67.9 g (0.27 mol) of methyl 3-(3-methyl-2-butenylthio)-2-methyl-benzoate in 600 ml of methylene chloride and the mixture was subsequently stirred at 0° C. for 3 hours. The reaction mixture was then poured into a mixture of 1.5 kg of ice and 500 ml of saturated ammonium chloride solution, and the phases that formed were separated. The organic phase was dried and the solvent was removed. The resulting orange oil (62.9 g) was used directly for the next step. For characterization, a sample was chromatographed over silica gel using ethyl acetate/cyclohexane (1:10). Melting point: 63° C.

Step c) Methyl 4,4,8-trimethyl-1,1-dioxothiochromane-7-carboxylate 30.7 g (0.12 mol) of methyl 4,4,8-trimethylthiochromane-7-carboxylate and a spatula tip of sodium tungstate were dissolved in 400 ml of glacial acetic acid and, at 50° C., 31.7 g (0.28 mol) of 30% strength hydrogen peroxide were added dropwise. The mixture was stirred at this temperature for another 5 hours and subsequently poured into ice water. The precipitated crystals were filtered off with suction, washed with water and dried. Yield: 31.8 g (91%); Melting point: 151° C.

Step d) Methyl 4,4-dimethyl-8-bromomethyl-1,1-dioxothiochromane-7-carboxylate

A little at a time, 20.5 g (0.12 mol) of N-bromosuccinimide were added with UV irradiation to a solution of 31 g (0.11 mol) of methyl 4,4,8-trimethyl-1,1-dioxothiochromane-7-carboxylate in 300 ml of acetonitrile at reflux temperature. At this temperature and under UV light, the mixture was stirred for another 1.5 hours and then poured into ice water. The residue was filtered off with suction, washed with water and dried.

Yield: 36.4 g (92%); Melting point: 163–165° C.

Step e): Propyl 4,4-dimethyl-8-propoxymethyl-1,1-dioxothiochromane-7-carboxylate (compound 3.12)

0.38 g (16.6 mmol) of sodium was added to 50 ml of propanol. After a clear solution had formed, 5.0 g (13.7 mmol) of methyl 4,4-dimethyl-8-bromomethyl-1,1-dioxothiochromane-7-carboxylate were added, and the mixture was stirred under reflux for 5 hours. After cooling, the solvent was distilled off and the residue was taken up in a 1:2 mixture of ethyl acetate and water. The organic phase was separated off, dried and concentrated.

Yield: 4.2 g; Melting point: 122–124° C.

Step f): 4,4-Dimethyl-8-propoxymethyl-1,1-dioxothiochromane-7-carboxylic acid (compound 3.13)

0.64 g (15.9 mmol) of sodium hydroxide was added to a solution of 3.9 g (10.6 mmol) of propyl 4,4-dimethyl-8-propoxymethyl-1,1-dioxothiochromane-7-carboxylate in a methanol/water mixture, and the reaction mixture was heated under reflux for 4 hours. After cooling, the organic solvent was removed and the residue was taken up in water and acidified with 2N hydrochloric acid. The precipitate that formed was filtered off with suction and dried.

Yield: 3.1 g; $^1$H-NMR (d$^6$-DMSO): δ (in ppm)=7.65 (s, 2H); 5.02 (s, 2H); 3.58 (m, 2H); 3.32 (m, 2H); 2.24 (m, 2H); 1.46 (q, 2H); 1.38 (s, 6H); 0.84 (t, 3H).

Step g): 4-{(4,4-Dimethyl-8-propoxymethyl-1,1-dioxothiochroman-7-yl)carbonyl}-5-hydroxy-1-methylpyrazole (compound 5 2.17)

A solution of 0.6 g (1.84 mmol) of 4,4-dimethyl-8-propoxymethyl-1,1-dioxothiochromane-7-carboxylic acid, 0.18 g (1.84 mmol) of 1-methyl-5-hydroxypyrazole and 0.38 g (1.84 mmol) of N,N-dicyclohexylcarbodiimide in 20 ml of acetonitrile was stirred at room temperature for 12 hours. The reaction mixture was subsequently stirred into a mixture of ethyl acetate and 2% strength aqueous sodium carbonate solution, and the precipitate which formed was filtered off with suction. The organic phase of the filtrate was dried and the solvent was distilled off. The resulting residue was dissolved in 5 ml of 1,4-dioxane, 0.51 g (3.7 mmol) of potassium carbonate were added and the mixture was heated under reflux for 4 hours. After cooling, the reaction mixture was taken up in ethyl acetate/water, and the aqueous phase was adjusted to pH 3 using 2N hydrochloric acid and subsequently extracted with ethyl acetate. The extract was dried and the solvent was removed, giving a solid.

Yield: 0.50 g; Melting point: 84° C.

2. 5-Methoxymethyl-1,1,4,4-tetraoxo-2,3-dihydro-1,4-benzodithiine-6-carboxylic acid (compound 3.31)

Step a) 6-methoxycarbonyl-5-methyl-1,4-dithia-spiro[4,5]-decane

Initially 41.0 g (436 mmol) of 1,2-dimercaptoethane and then 6.8 ml of boron trifluoride etherate were added dropwise to a solution of 49.4 g (291 mmol) of methyl 2-methyl-3-oxocyclohexanecarboxylate (prepared according to Gupla et al., J. Sci. Ind. Res. B, 1962, 21, 219) in 200 ml methylene chloride, and the mixture was stirred at room temperature overnight. 200 ml of 2N aqueous sodium hydroxide solution were added, the phases were separated, the organic phase was dried over sodium sulfate and the solvent was removed.

Yield: 56.7 g (yellow oil).

Step b) Methyl 5-methyl-2,3-dihydro-1,4-benzodithiine-6-carboxylate

At −78° C., 177.59 g (982 mmol) of N-bromosuccinimide were added to 80.5 g (327 mmol) of 6-methoxycarbonyl-5-methyl-1,4-dithia-spiro[4,5]-decane in 1200 ml of methylene chloride, and the mixture was stirred at this temperature for 30 minutes. The mixture was allowed to warm to room temperature and filtered through silica gel. The filtrate was washed successively with 10% strength sodium bicarbonate solution and 10% strength sodium hydrogen sulfite solution, dried over sodium sulfate and concentrated. The residue was subsequently dissolved in 500 ml of dimethylsulfoxide and added dropwise to 14.8 g (390 mmol) of sodium boranate in 200 ml of dimethylsulfoxide. The mixture was stirred for 3 hours, and 100 ml of water were then added dropwise. The mixture was extracted with ethyl acetate and dried over sodium sulfate, and the solvent was removed.

Yield: 54.5 g (yellow oil); $^1$H-NMR(CDCl$_3$): δ (in ppm)=7.45 (d, 1H); 7.05 (d, 1H); 3.84 (s, 3H); 3.37–3.20 (m, 4H); 2.52 (s, 3H).

Step c) Methyl 5-methyl-1,1,4,4-tetraoxo-2,3-dihydro-1,4-benzodithiine-6-carboxylate At 50–60° C., 208 g (1830 mmol) of a 30% strength hydrogen peroxide solution were added dropwise to 100 g (420 mmol) of methyl 5-methyl-2,3-dihydro-1,4-benzodithiine-6-carboxylate in 500 ml of glacial acetic acid and a spatula tip of sodium tungstate, and the mixture was stirred at 50° C. for 3 hours. The mixture was then poured into water and the resulting precipitate was filtered off with suction. The product was washed successively with sodium bisulfite solution and water and dried under reduced pressure.

Yield: 123 g (colorless solid); $^1$H-NMR (d$^6$-DMSO): δ (in ppm)=8.10 (d, 1H); 8.04 (d, 1H); 4.42 (m, 4H); 3.90 (s, 3H); 2.75 (s, 3H).

Step d) Methyl 5-bromomethyl-1,1,4,4-tetraoxo-2,3-dihydro-1,4-benzodithiine-6-carboxylate Under reflux and with UV irradiation, 12.9 g (73 mmol) of N-bromosuccinimide were added a little at a time to a suspension of 21 g (69 mmol) of methyl 5-methyl-1,1,4,4-tetraoxo-2,3-dihydro-1,4-benzodithiine-6-carboxylate in 200 ml of acetonitrile. After another 6 hours under the abovementioned conditions, the solvent was removed, the residue was stirred with water and the precipitate was filtered off with suction and dried.

Yield: 24.3 g; Melting point: 188° C. (with decomposition).

Step e) Methyl 5-methoxymethyl-1,1,4,4-tetraoxo-2,3-dihydrobenzodithiin-6-carboxylate (compound 3.30)

At room temperature, 2.35 g (13 mmol) of sodium methoxide in methanol (30% strength solution) were added dropwise to a solution of 5.0 g (13 mmol) of methyl 5-bromomethyl-1,1,4,4-tetraoxo-2,3-dihydro-1,4-benzodithiine-6-carboxylate in 50 ml of methanol, and the mixture was subsequently heated to 40° C. After 30 minutes, the solvent was removed, the residue was stirred with water and the aqueous phase was extracted with ethyl acetate. The solvent was removed and the residue was then chromatographed over silica gel.

Yield: 1.4 g (colorless solid); $^1$H-NMR(CDCl$_3$): δ (in ppm)=8.40 (d, 1H); 8.08 (d, 1H); 6.25 (d, 1H); 6.07 (d, 1H); 4.02 (s, 3H); 3.94–3.42 (m, 4H); 3.18 (s, 3H).

Step f) 5-methoxymethyl-1,1,4,4-tetraoxo-2,3-dihydro-1,4-benzodithiine-6-carboxylic acid (compound 3.31)

A solution of 1.3 g (3.9 mmol) of methyl 5-methoxymethyl-1,1,4,4-tetraoxo-2,3-dihydro-benzodithiine-6-carboxylate in a 1:1 mixture of methanol/water was mixed with 0.23 g (5.8 mmol) of sodium hydroxide and heated under reflux for 1 hour. The solvent was removed and the residue was taken up in water and acidified with 2N hydrochloric acid. The resulting crystalline precipitate was filtered off with suction and dried.

Yield: 0.8 g (colorless solid); $^1$H-NMR(d$^6$-DMSO): δ (in ppm)=8.40 (d, 1H); 8.18 (d, 1H); 6.18 (d, 1H); 6.08 (d, 1H); 3.80–3.60 (m, 4H); 3.02 (s, 3H).

In addition to the abovementioned thiochromanoylpyrazolone derivative of the formula I and the carboxylic acid derivatives of the formula IV, other compounds which were prepared and are preparable in an analogous manner are listed in Tables 2 and 3 below:

TABLE 2

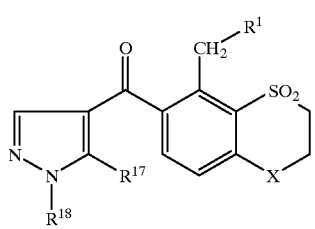

Ia (where A = CH$_2$, R$^3$, R$^{19}$ = H, m = 2, n = 0)

| No. | R$^1$ | X | R$^{17}$ | R$^{18}$ | m.p. [° C.] |
|---|---|---|---|---|---|
| 2.1 | SCH$_3$ | C(CH$_3$)$_2$ | OH | CH$_3$ | 233 |
| 2.2 | SCH$_3$ | C(CH$_3$)$_2$ | OH | CH$_2$CH$_3$ | 205 |
| 2.3 | SO$_2$CH$_3$ | C(CH$_3$)$_2$ | OH | CH$_3$ | 196–197 |
| 2.4 | SO$_2$CH$_3$ | C(CH$_3$)$_2$ | OH | CH$_2$CH$_3$ | 173–175 |
| 2.5 | S(CH$_2$)$_2$CH$_3$ | C(CH$_3$)$_2$ | OH | CH$_3$ | 187–188 |
| 2.6 | S(CH$_2$)$_2$CH$_3$ | C(CH$_3$)$_2$ | OH | CH$_2$CH$_3$ | 163 |
| 2.7 | SO(CH$_2$)$_2$CH$_3$ | C(CH$_3$)$_2$ | OH | CH$_3$ | 250 |
| 2.8 | SO(CH$_2$)$_2$CH$_3$ | C(CH$_3$)$_2$ | OH | CH$_2$CH$_3$ | 250 |
| 2.9 | SCH(CH$_3$)$_2$ | C(CH$_3$)$_2$ | OH | CH$_3$ | 163–165 |
| 2.10 | SCH(CH$_3$)$_2$ | C(CH$_3$)$_2$ | OH | CH$_2$CH$_3$ | 163–165 |
| 2.11 | SO$_2$CH(CH$_3$)$_2$ | C(CH$_3$)$_2$ | OH | CH$_3$ | 125–127 |
| 2.12 | SO$_2$CH(CH$_3$)$_2$ | C(CH$_3$)$_2$ | OH | CH$_2$CH$_3$ | 96–98 |
| 2.13 | S-(benz-thiazol-2-yl) | C(CH$_3$)$_2$ | OH | CH$_3$ | 215 |
| 2.14 | S-(benz-thiazol-2-yl) | C(CH$_3$)$_2$ | OH | CH$_2$CH$_3$ | 288 (decomp.) |
| 2.15 | OCH$_3$ | C(CH$_3$)$_2$ | OH | CH$_3$ | >250 |
| 2.16 | OCH$_3$ | C(CH$_3$)$_2$ | OH | CH$_2$CH$_3$ | 222–223 |
| 2.17 | O(CH$_2$)$_2$CH$_3$ | C(CH$_3$)$_2$ | OH | CH$_3$ | 84 |
| 2.18 | O(CH$_2$)$_2$CH$_3$ | C(CH$_3$)$_2$ | OH | CH$_2$CH$_3$ | 154–156 |
| 2.19 | P(O)(OCH$_2$CH$_3$)$_2$ | C(CH$_3$)$_2$ | OH | CH$_3$ | 183–185 |
| 2.20 | SO$_2$(CH$_2$)$_3$CH$_3$ | C(CH$_3$)$_2$ | OH | CH$_3$ | 101–104 |
| 2.21 | SO$_2$(CH$_2$)$_3$CH$_3$ | C(CH$_3$)$_2$ | OH | CH$_2$CH$_3$ | 89–91 |
| 2.22 | SO$_2$CH$_2$CH$_3$ | C(CH$_3$)$_2$ | OH | CH$_3$ | 177 |
| 2.23 | SO$_2$CH$_2$CH$_3$ | C(CH$_3$)$_2$ | OH | CH$_2$CH$_3$ | 194–197 |
| 2.24 | OCH$_2$CF$_3$ | C(CH$_3$)$_2$ | OH | CH$_3$ | 185–187 |
| 2.25 | OCH$_2$CF$_3$ | C(CH$_3$)$_2$ | OH | CH$_2$CH$_3$ | 178 |
| 2.26 | OCH$_2$CH$_2$F | C(CH$_3$)$_2$ | OH | CH$_3$ | 194–195 |
| 2.27 | OCH$_2$CH$_2$F | C(CH$_3$)$_2$ | OH | CH$_2$CH$_3$ | 184–185 |

TABLE 3

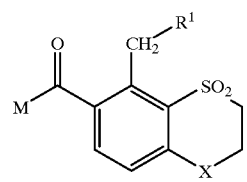

(where A = CH$_2$, R$^3$ = H, m = 2, n = 0)

| No. | R$^1$ | M | X | m.p. [° C.] or $^1$H-NMR [δ in ppm] |
|---|---|---|---|---|
| 3.1 | SCH$_3$ | OCH$_3$ | C(CH$_3$)$_2$ | 7.80(d, 1H); 7.40 (d, 1H); 4.68(s, 2H); 3.91(s, 3H); 3.45(m, 2H); 2.35 (m, 2H); 2.08(s, 3H); 1.43(s, 6H); |
| 3.2 | SCH$_3$ | OH | C(CH$_3$)$_2$ | 7.84(d, 1H); 7.64 (d, 1H); 4.58(s, 2H); 3.60(m, 2H); 2.22(m, 2H); 1.96 (s, 3H); 1.38(s, 6H); |
| 3.3 | SO$_2$CH$_3$ | OH | C(CH$_3$)$_2$ | 223 |
| 3.4 | S(CH$_2$)$_2$CH$_3$ | OCH$_3$ | C(CH$_3$)$_2$ | 87 |
| 3.5 | S(CH$_2$)$_2$CH$_3$ | OH | C(CH$_3$)$_2$ | 163–166 |
| 3.6 | SO$_2$(CH$_2$)$_2$CH$_3$ | OH | C(CH$_3$)$_2$ | 158–160 |
| 3.7 | SCH(CH$_3$)$_2$ | OCH$_3$ | C(CH$_3$)$_2$ | 79–80 |
| 3.8 | SCH(CH$_3$)$_2$ | OH | C(CH$_3$)$_2$ | 191–192 |
| 3.9 | SO$_2$CH(CH$_3$)$_2$ | OH | C(CH$_3$)$_2$ | 239–240 |
| 3.10 | OCH$_3$ | OCH$_3$ | C(CH$_3$)$_2$ | 131–133 |
| 3.11 | OCH$_3$ | OH | C(CH$_3$)$_2$ | 227–229 |
| 3.12 | O(CH$_2$)$_2$CH$_3$ | O(CH$_2$)$_2$CH$_3$ | C(CH$_3$)$_2$ | 7.66(d, 1H); 7.42 (s, 1H); 5.20(s, 2H); 4.24(t, 2H); 3.40(m, 4H); 2.36 (m, 2H)1.78(m, 2H); 1.53(m, 2H); 1.40(s, 6H); 1.00 (t, 3H); 0.85(t, 3H); |
| 3.13 | O(CH$_2$)$_2$CH$_3$ | OH | C(CH$_3$)$_2$ | 145 |
| 3.14 | pyrazol-1-yl | OCH$_3$ | C(CH$_3$)$_2$ | 171 |
| 3.15 | pyrazol-1-yl | OH | C(CH$_3$)$_2$ | 179 |
| 3.16 | 1,2,4-triazol-1-yl | OCH$_3$ | C(CH$_3$)$_2$ | 8.26(s, 1H); 7.90 (d, 1H); 7.85(s, 1H); 7.55(d, 1H); 6.33(s, 2H); 3.92 (s, 3H); 3.52(m, 2H); 2.38(m, 2H); 1.46(s, 6H); |
| 3.17 | 1,2,4-triazol-1-yl | OH | C(CH$_3$)$_2$ | 265 |
| 3.18 | morpholin-4-yl | OCH$_3$ | C(CH$_3$)$_2$ | 208–210 |
| 3.19 | morpholin-4-yl | OH | C(CH$_3$)$_2$ | 224 |
| 3.20 | S-benzthiazol-2-yl | OCH$_3$ | C(CH$_3$)$_2$ | 137–138 |
| 3.21 | S-benzthiazol-2-yl | OH | C(CH$_3$)$_2$ | 108–109 |
| 3.22 | P(O)(OCH$_2$CH$_3$)$_2$ | OCH$_3$ | C(CH$_3$)$_2$ | 7.89(d, 1H); 7.40 (d, 1H); 4.50(d, 2H); 4.12(m, 2H); 4.06(m, 2H); 3.97 (s, 3H); 3.42(m, 2H); 2.38(m, 2H); 1.42(s, 6H); 1.24 (t, 6H); |
| 3.23 | P(O)(OCH$_2$CH$_3$)$_2$ | OH | C(CH$_3$)$_2$ | 139–142 |
| 3.24 | SCH$_2$CH$_3$ | OCH$_3$ | C(CH$_3$)$_2$ | 128–137 |
| 3.25 | SCH$_2$CH$_3$ | OH | C(CH$_3$)$_2$ | 205–208 |
| 3.26 | S(CH$_2$)$_3$CH$_3$ | OCH$_3$ | C(CH$_3$)$_2$ | 7.80(d, 1H); 7.38 (d, 1H); 4.68(s, 2H); 3.90(s, 3H); 3.44(m, 2H); 2.56 (t, 2H); 2.36(m, 2H); 1.40(m, 10H); 0.85(t, 3H); |
| 3.27 | SO$_2$CH$_2$CH$_3$ | OH | C(CH$_3$)$_2$ | 230 |
| 3.28 | S(CH$_2$)$_3$CH$_3$ | OH | C(CH$_3$)$_2$ | 81–83 |
| 3.29 | SO$_2$(CH$_2$)$_3$CH$_3$ | OH | C(CH$_3$)$_2$ | 180–182 |
| 3.30 | OCH$_3$ | OCH$_3$ | SO$_2$ | 8.40(d, 1H); 8.08 |

| | | | | |
|---|---|---|---|---|
| 3.31 | OCH$_3$ | OH | SO$_2$ | (d, 1H); 6.25(d, 1H); 4.02(s, 3H); 3.94–3.42(m, 4H), 3.18(s, 3H); 8.40(d, 1H); 8.18 (d, 1H); 6.18(d, 1H); 6.08(d, 1H); 3.80–3.60(m, 4H); 3.02(s, 3H); 203–205 |
| 3.32 | N(CH$_3$)(COCF$_3$) | OH | C(CH$_3$)$_2$ | 203–205 |
| 3.33 | N(CH$_3$)(COCF$_3$) | OCH$_3$ | C(CH$_3$)$_2$ | 140–143 |
| 3.34 | OCH$_2$CH$_2$F | OH | C(CH$_3$)$_2$ | 167–168 |
| 3.35 | OCH$_2$CH$_2$F | OCH$_3$ | C(CH$_3$)$_2$ | 101(decomp.) |
| 3.36 | NO$_2$ | OCH$_3$ | C(CH$_3$)$_2$ | 154–157 |
| 3.37 | SO$_2$CH$_2$CH=CH$_2$ | OH | C(CH$_3$)$_2$ | 63 |
| 3.38 | SCH$_2$CH=CH$_2$ | OH | C(CH$_3$)$_2$ | 170–173 |
| 3.39 | SCH$_2$CH=CH$_2$ | OCH$_3$ | C(CH$_3$)$_2$ | 134 |
| 3.40 | OCH$_2$CF$_3$ | OH | C(CH$_3$)$_2$ | 184–186 |
| 3.41 | OCH$_2$CF$_3$ | OCH$_3$ | C(CH$_3$)$_2$ | 94–95 |
| 3.42 | OCH(CH$_3$)$_2$ | OH | C(CH$_3$)$_2$ | 142–144 |
| 3.43 | S-(1,2,3-triazol-5-yl) | OCH$_3$ | C(CH$_3$)$_2$ | 59 |
| 3.44 | N(CH$_2$CH=CH$_2$)$_2$ | OH | C(CH$_3$)$_2$ | 85 |
| 3.45 | N(CH$_2$CH=CH$_2$)$_2$ | OCH$_3$ | C(CH$_3$)$_2$ | 69 |
| 3.46 | N(CH$_3$) | OCH$_3$ | C(CH$_3$)$_2$ | 116 |
| 3.47 | N(CH$_2$CH$_2$CH$_3$)$_2$ | OCH$_3$ | C(CH$_3$)$_2$ | 7.50(d, 1H); 7.36 (d, 1H); 4.24(s, 2H); 3.80(s, 3H); 3.40(m, 2H); 2.35 (m, 6H); 1.40(s, 6H); 0.76(t, 6H); |
| 3.48 | S(CH$_2$)$_2$CH$_3$ | OH | C=O | 142–144 |
| 3.49 | SCH$_3$ | OCH$_3$ | C=O | 117–118 |

The compounds of the formula I and their agriculturally useful salts are suitable for use as herbicides, both in the form of isomer mixtures and in the form of the pure isomers. The herbicidal compositions which comprise compounds of the formula I effect very good control of vegetation on non-crop areas, especially at high rates of application. In crops such as wheat, rice, maize, soya and cotton, they act against weeds and grass weeds without inflicting substantial damage to the crop plants. This effect is observed mainly at low rates of application.

Depending on the application method in question, the compounds of the formula I, or herbicidal compositions comprising them, can also be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa, Musa* spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds of the formula I can also be used in crops which, by means of breeding, including genetic engineering methods, have been made tolerant to the action of herbicides.

The compounds of the formula I, or the herbicidal compositions comprising them, can be used, for example, in the form of directly sprayable aqueous solutions, powders, suspensions, also highly concentrated aqueous, oily or other suspensions or dispersions, emulsions, oil dispersions, pastes, dusts, materials for spreading, or granules, by means of spraying, atomizing, dusting, spreading or pouring. The use forms depend on the intended purposes; in any case, they should guarantee the finest possible distribution of the active ingredients according to the invention.

The herbicidal compositions comprise a herbicidally effective amount of at least one compound of the formula I or an agriculturally useful salt of I and auxiliaries which are customary for the formulation of crop protection agents.

Suitable inert auxiliaries are essentially:

mineral oil fractions of medium to high boiling point such as kerosine and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the thiochromanoylpyrazolone derivatives of the formula I, as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and these concentrates are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active substances together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise approximately from 0.001 to 98% by weight, preferably from 0.01 to 95% by weight, of at least one active ingredient. The active ingredients are employed in a purity of from 90% to 100%, preferably 95% to 100% (in accordance with NMR spectra).

The formulation examples which follow illustrate the preparation of such products:

I. 20 parts by weight of compound No. 2.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of compound No. 2.3 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of compound No. 2.7 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of compound No. 2.16 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of compound No. 2.23 are mixed with 97 parts by weight of finely divided kaolin. This gives a dust which comprises 3% by weight of the active ingredient.

VI. 20 parts by weight of compound No. 2.24 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of compound No. 2.19 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of compound No. 2.15 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I, or the herbicidal compositions, may be applied pre- or post-emergence. If the active ingredients are less well tolerated by certain crop plants, application techniques may be used in which the herbicidal compositions are sprayed, with the aid of the spraying equipment, in such a way that they come in as little contact as possible, if any, with the leaves of the sensitive crop plants while reaching the leaves of undesirable plants which grow underneath, or the bare soil surface (post-directed, lay-by).

Depending on the control target, the season, the target plants and the growth stage, the rates of application of compound of the formula I are from 0.001 to 3.0, preferably 0.01 to 1.0, kg of active substance (a.s.) per ha.

To widen the spectrum of action and to achieve synergistic effects, the thiochromanoylpyrazolone derivatives of the formula I may be mixed with a large number of representatives of other groups of herbicidal or growth-regulating active ingredients and applied jointly. Suitable components for mixtures are, for example, 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothiadiazinones, 2-aroyl-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Furthermore, it may be advantageous to apply the compounds of the formula I, alone or in combination with other herbicides, also as a mixture with other crop protection agents, for example with pesticides or agents for controlling phytopathogenic fungi or bacteria. Also of interest is the miscibility with mineral salt solutions which are employed for remedying nutritional and trace-element deficiencies. Nonphytotoxic oils and oil concentrates may also be added.

USE EXAMPLES

The herbicidal activity of the thiochromanoylpyrazolone derivatives of the formula I was demonstrated by the following greenhouse experiments:

the culture containers used were plastic flowerpots containing loamy sand with approximately 3.0% of humus as the substrate. The seeds of the test plants were sown separately for each species.

In the case of the pre-emergence treatment, the active ingredients, which were suspended or emulsified in water, were planted directly after sowing by means of finely distributing nozzles. The containers were irrigated gently to promote germination and growth and subsequently covered with transparent plastic hoods until the plants rooted. This cover caused uniform germination of the test plants unless this was adversely affected by the active ingredients.

For the post-emergence treatment, the test plants were first grown to a plant height of from 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The application rate for the post-emergence treatment was 0.25 or 0.125 kg of a.s. (active substance) per ha.

Depending on the species, the plants were kept at from 10 to 25° C. or from 20 to 35° C. The test period extended over 2 to 4 weeks. During this time, the plants were tended and their response to the individual treatments was evaluated.

Evaluation was carried out using a scale from 0 to 100. 100 means no emergence of the plants, or complete destruction of at least the above-ground parts, and 0 means no damage or normal course of growth.

The plants used in the greenhouse experiments belonged to the following species:

| Scientific Name | Common name |
| --- | --- |
| Avena fatua | wild oat |
| Echinocloa crus-gali | common barnyard-grass |
| Chenopodium album | lambsquarter |
| Ipomoea ssp. | morning glory |
| Polygonum persicaria | redshank |
| Setaria viridis | bottlegrass |
| Sinapis alba | white mustard |
| Solanum nigrum | black nightshade |
| Triticum aestivum | spring wheat |
| Veronica ssp. | speadwell |

At application rates of 0.25 or 0.125 kg/ha, the compound 2.3 had very good post-emergence activity against the harmful plants *Echinocloa crus-gali*, *Ipomoea* spp., *Solanum nigrum* and *Veronica* ssp., and it was at the same time compatible with the crop plant *Triticum aestivum*. Furthermore, the compound 2.17 had very good activity against the weeds *Avena fatua, Setaria viridis, Polygonum persicaria* and *Sinapis alba*.

We claim:

1. A thiochromanoylpyrazolone derivative of the formula I:

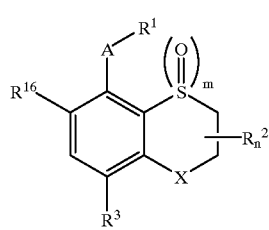

where:
A is $C_1$–$C_6$-alkanediyl, $C_2$–$C_6$-alkenediyl, $C_4$–$C_6$-alkadienediyl or $C_2$–$C_6$-alkynediyl, where the above-mentioned radicals may carry one or two substituents from the following group: cyano, $C_1$–$C_4$-alkoxy, $C_1$–$C_4$-alkylthio, $C_1$–$C_4$-alkylcarbonyl or $C_1$–$C_4$-alkoxycarbonyl;

$R^1$ is cyano, thiocyanato, nitro, $OR^4$, $SR^5$, $SOR^6$, $SO_2R^6$, $ONR^6R^7$, $ON=CR^6R^8$, $NR^9R^{10}$, $P(O)R^{11}R^{12}$, $P(S)R^{11}R^{12}$, $COR^6$, $CO_2R^6$, phenyl, heterocyclyl or N-bonded heterocyclyl, where the three last-mentioned radicals for their part may be partially or fully halogenated and/or may carry one to three substituents from the following group: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^2$ is $C_1$–$C_6$-alkyl, $C_1$–$C_6$-haloalkyl, $C_1$–$C_6$-alkoxy or $C_1$–$C_6$-haloalkoxy;

$R^3$ is hydrogen, halogen or $C_1$–$C_6$-alkyl;

X is oxygen, sulfur, S=O, S(=O)$_2$, $CR^{13}R^{14}$, C=O or C=$NR^{15}$;

m is 0, 1 or 2;

n is 0, 1, 2, 3 or 4;

$R^4$, $R^5$ are one of the radicals mentioned under $R^6$;

are hydrogen, $C_1$–$C_4$-alkylcarbonyl, $C_1$–$C_4$-haloalkylcarbonyl, $C_1$–$C_4$-alkoxycarbonyl, $C_1$–$C_4$-haloalkoxycarbonyl, $C_1$–$C_4$-alkylsulfonyl, $C_1$–$C_4$-haloalkylsulfonyl, $P(O)R^{11}R^{12}$ or $P(S)R^{11}R^{12}$;

are phenylcarbonyl, phenoxycarbonyl, phenyl-$C_1$–$C_4$-alkylcarbonyl, phenylsulfonyl, phenoxysulfonyl, heterocyclylcarbonyl, heterocyclyloxycarbonyl, heterocyclyl-$C_1$–$C_4$-alkylcarbonyl, heterocyclylsulfonyl or heterocyclyloxysulfonyl, where the phenyl and the heterocyclyl radical of the ten last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^6$ is $C_1$–$C_6$-alkyl, $C_3$–$C_6$-alkenyl, $C_3$–$C_6$-alkinyl or $C_3$–$C_6$-cycloalkyl, where the four abovementioned radicals may be partially or fully halogenated and/or may carry one to three of the following groups:

cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl, $C_1$–$C_4$-alkylcarbonyl, $C_1$–$C_4$-alkoxycarbonyl and $C_1$–$C_4$-haloalkoxycarbonyl;

is phenyl, phenyl-$C_1$–$C_4$-alkyl, heterocyclyl or heterocyclyl-$C_1$–$C_4$-alkyl, where the phenyl and the heterocyclyl radical of the four last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^7$ is hydrogen or $C_1$–$C_6$-alkyl;

$R^8$ is hydrogen, $C_1$–$C_6$-alkyl, $C_1$–$C_6$-alkoxycarbonyl, cyano or $C_1$–$C_6$-alkoxy;

$R^9$ is one of the radicals mentioned under $R^4$;

is $C_1$–$C_6$-alkoxy, $C_3$–$C_6$-alkenyloxy, $C_3$–$C_6$-alkinyloxy, aminocarbonyl, N—$C_1$–$C_6$-alkylaminocarbonyl or N,N-di-($C_1$–$C_6$-alkyl) aminocarbonyl;

$R^{10}$ is hydrogen, $C_1$–$C_6$-alkyl, $C_3$–$C_6$-alkenyl or $C_3$–$C_6$-alkinyl;

$R^{11}$, $R^{12}$ are hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{13}$, $R^{14}$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, N—$C_1$–$C_6$-alkylamino, N—$C_1$–$C_6$-haloalkylamino, N,N—(di-$C_1$–$C_6$-alkyl)amino, N—$C_1$–$C_6$-alkoxyamino, N—($C_1$–$C_6$-alkoxy)—N—($C_1$–$C_6$-alkyl)amino, 1-tetrahydropyrrolyl, 1-piperidinyl, 4-morpholinyl or 1-hexahydropyrazinyl;

or $R^{13}$, $R^{14}$ together form a methylidene group which may be substituted by one or two substituents from the following group: halogen, cyano, $C_1$–$C_6$-alkyl, $C_1$–$C_6$-haloalkyl, $C_1$–$C_6$-alkoxy or $C_1$–$C_6$-haloalkoxy;

$R^{15}$ is $C_1$–$C_6$-alkyl, $C_1$–$C_6$-haloalkyl, $C_1$–$C_6$-alkoxy or $C_1$–$C_6$-haloalkoxy;

$R^{16}$ is a radical IIa or IIb,

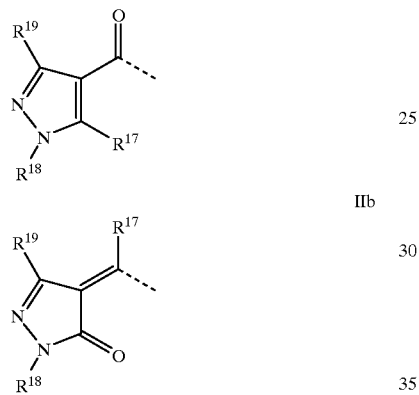

IIa

IIb where:
$R^{17}$ is hydroxyl, mercapto, halogen, $OR^{20}$, $SR^{20}$, $SOR^{21}$, $SO_2R^{21}$, $OSO_2R^{21}$, $P(O)R^{22}R^{23}$, $OP(O)R^{22}R^{23}$, $P(S)R^{22}R^{23}$, $OP(S)R^{22}R^{23}$, $NR^{24}R^{25}$, $ONR^{21}R^{21}$ or N-bonded heterocyclyl which may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{18}$ is hydrogen, $C_1$–$C_6$-alkyl, $C_1$–$C_6$-haloalkyl, hydroxyl, $C_1$–$C_6$-alkoxy or $C_1$–$C_6$-haloalkoxy;

$R^{19}$ is hydrogen, halogen, $C_1$–$C_6$-alkyl, $C_1$–$C_6$-haloalkyl, hydroxyl, $C_1$–$C_6$-alkoxy, $C_1$–$C_6$-haloalkoxy, $C_1$–$C_6$-alkylthio or $C_1$–$C_6$-haloalkylthio;

$R^{20}$ is $C_1$–$C_6$-alkyl, $C_3$–$C_6$-alkenyl, $C_3$–$C_6$-haloalkenyl, $C_3$–$C_6$-alkinyl, $C_3$–$C_6$-haloalkinyl, $C_3$–$C_6$-cycloalkyl, $C_1$–$C_6$-alkylcarbonyl, $C_2$–$C_6$-alkenylcarbonyl, $C_2$–$C_6$-alkinylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkinyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkinylaminocarbonyl, N,N-di-($C_1$–$C_6$-alkyl)aminocarbonyl, N—($C_3$–$C_6$-alkenyl)—N—($C_1$–$C_6$-alkyl)aminocarbonyl, N—($C_3$–$C_6$-alkinyl)—N—($C_1$–$C_6$-alkyl)aminocarbonyl, N—($C_1$–$C_6$-alkoxy)—N—($C_1$–$C_6$-alkyl)aminocarbonyl, N—($C_3$–$C_6$-alkenyl)—N—($C_1$–$C_6$-alkoxy)aminocarbonyl, N—($C_3$–$C_6$-alkinyl)—N—($C_1$–$C_6$-alkoxy)aminocarbonyl, di-($C_1$–$C_6$-alkyl)aminothiocarbonyl or $C_1$–$C_6$-alkoxyimino-$C_1$–$C_6$-alkyl, where the abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenyl, phenyl-$C_1$–$C_6$-alkyl, phenylcarbonyl-$C_1$–$C_6$-alkyl, phenylcarbonyl, phenoxycarbonyl, phenyloxythiocarbonyl, phenylaminocarbonyl, N—($C_1$–$C_6$-alkyl)—N—(phenyl)aminocarbonyl, phenyl-$C_2$–$C_6$-alkenylcarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, heterocyclylaminocarbonyl, N—($C_1$–$C_6$-alkyl)—N—(heterocyclyl)aminocarbonyl or heterocyclyl-$C_2$–$C_6$-alkenylcarbonyl, where the phenyl and the heterocyclyl radical of the 18 last mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{21}$ is $C_1$–$C_6$-alkyl, $C_3$–$C_6$-alkenyl, $C_3$–$C_6$-alkinyl or $C_3$–$C_6$-cycloalkyl, where the four abovementioned radicals may be partially or fully halogenated and/or may carry one to three of the following groups: cyano, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl or $C_1$–$C_4$-haloalkoxycarbonyl;

is phenyl, phenyl-$C_1$–$C_6$-alkyl, heterocyclyl or heterocyclyl-$C_1$–$C_6$-alkyl, where the phenyl and the heterocyclyl radical of the last mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{22}$, $R^{23}$ is hydrogen, hydroxyl, $C_1$–$C_6$-alkyl, $C_1$–$C_6$-alkoxy, $C_1$–$C_6$-alkylthio, phenyl, phenyl-$C_1$–$C_4$-alkyl or phenoxy, where the three last-mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^{24}$ is hydrogen, $C_1$–$C_6$-alkyl, $C_3$–$C_6$-alkenyl, $C_3$–$C_6$-haloalkenyl, $C_3$–$C_6$-alkinyl, $C_3$–$C_6$-haloalkinyl, $C_3$–$C_6$-cycloalkyl, $C_1$–$C_6$-alkylcarbonyl, hydroxyl, $C_1$–$C_6$-alkoxy, $C_3$–$C_6$-alkenyloxy, $C_3$–$C_6$-alkinyloxy, amino, $C_1$–$C_6$-alkylamino, di-($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three of the following radicals: cyano, $C_1$–$C_4$-alkoxycarbonyl, $C_1$–$C_4$-alkylaminocarbonyl, di-($C_1$–$C_4$-alkyl)aminocarbonyl or $C_3$–$C_6$-cycloalkyl;

is phenyl, phenyl-$C_1$–$C_4$-alkyl, phenylcarbonyl, heterocyclyl, heterocyclyl-$C_1$–$C_4$-alkyl or heterocyclylcarbonyl, where the phenyl or heterocyclyl radical of the six last mentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{25}$ is hydrogen, $C_1$–$C_6$-alkyl, $C_3$–$C_6$-alkenyl or $C_3$–$C_6$-alkinyl;

and its agriculturally useful salts.

2. A process for preparing compounds of the formula I where $R^{17}$=hydroxyl, as claimed in claim 1, which comprises acylating a pyrazolone of the formula III;

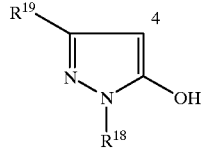

(III)

where the variables $R^{18}$ and $R^{19}$ are as defined in claim 1 with an activated carboxylic acid IVa or a carboxylic acid IVb

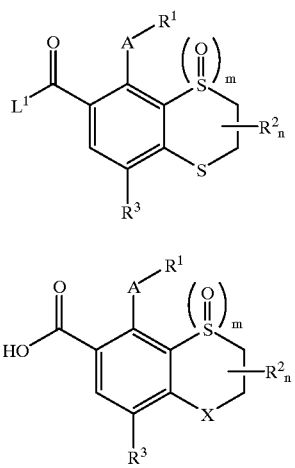

where the variables $R^1$ to $R^3$, A, X, m and n are as defined under claim 1 and $L^1$ is a nucleophilically replaceable leaving group, and rearranging the acylation product, if appropriate in the presence of a catalyst, to give the compounds I where $R^{17}$=hydroxyl.

3. A process for preparing compounds of the formula I as claimed in claim 1 where $R^{17}$=halogen, which comprises reacting a thiochromanoylpyrazolone derivative of the formula I where $R^{17}$=hydroxyl with a halogenating agent.

4. A process for preparing compounds of the formula I as claimed in claim 1 where $R^{17}$=$OR^{20}$, $OSO_2R^{21}$, $OP(O)R^{22}R^{23}$ or $OP(S)R^{22}R^{23}$, which comprises reacting a thiochromanoylpyrazolone derivative of the formula I where $R^{17}$=hydroxyl with an alkylating agent Vα, sulfonylating agent Vβ or phosphonylating agent Vγ or Vδ,

| $L^2$—$R^{20}$ | $L^2$—$SO_2R^{21}$ | $L^2$—$P(O)R^{22}R^{23}$ | $L^2$—$P(S)R^{22}R^{23}$ |
|---|---|---|---|
| Vα | Vβ | Vγ | Vδ | where the variables $R^{20}$ to $R^{23}$ are as defined in claim 1 and $L^2$ is a nucleophilically replaceable leaving group.

5. A process for preparing compounds of the formula I as claimed in claim 1 where $R^{17}$=$OR^{20}$, $SR^{20}$, $P(O)R^{22}R^{23}$, $NR^{24}R^{25}$, $ONR^{21}R^{21}$ or N-bonded heterocyclyl, which comprises reacting a thiochromanoylpyrazolone derivative of the formula I where $R^{17}$=halogen or $OSO_2R^{21}$ with a compound of the formula VIα, VIβ, VIγ, VIδ, VIε or VIη

| $HOR^{20}$ | $HSR^{20}$ | $HPOR^{22}R^{23}$ | $HNR^{24}R^{25}$ | $HONR^{21}R^{21}$ |
|---|---|---|---|---|
| VIα | VIβ | VIγ | VIδ | VIε |
| H(N-bonded heterocyclyl) | | | | |
| VIη | | | | | where the variables $R^{20}$ to $R^{25}$ are as defined in claim 1, if appropriate in the presence of a base.

6. A process for preparing compounds of the formula I as claimed in claim 1 where $R^{17}$=$SOR^{21}$, $SO_2R^{21}$, which comprises reacting a compound of the formula I where $R^{17}$=$SR^{21}$ with an oxidizing agent.

7. A process for preparing compounds of the formula I where $R^{16}$=IIa as claimed in claim 1, which comprises reacting a metallated pyrazole derivative of the formula VII where M is a metal and $R^{17}$ to $R^{19}$ are as defined in claim 1 with a carboxylic acid derivative of the formula IVa where $R^1$ to $R^3$, A, X, m and n are as defined in claim 1 and $L^1$ represents a nucleophilically replaceable leaving group

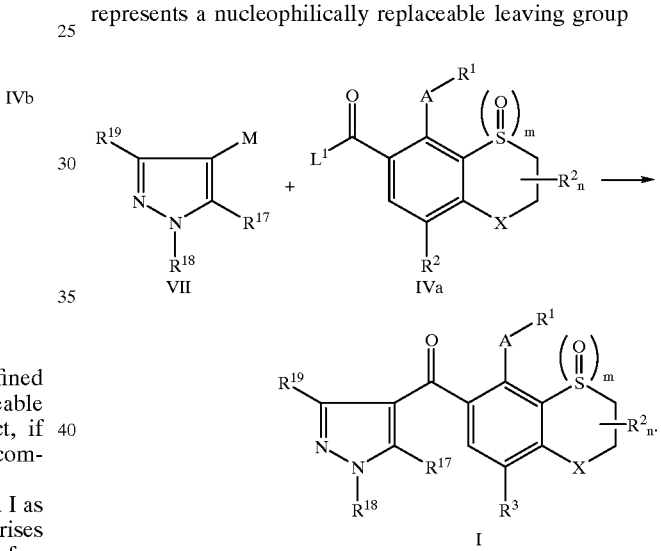

8. A composition, comprising a herbicidally effective amount of at least one thiochromanoylpyrazolone derivative of the formula I or an agriculturally useful salt of I as claimed in claim 1, and auxiliaries which are customarily used for formulating crop protection agents.

9. A process for preparing compositions as claimed in claim 8, which comprises mixing a herbicidally effective amount of at least one thiochromanoylpyrazolone derivative of the formula I or an agriculturally useful salt of I and auxiliaries which are customarily used for formulating crop protection agents.

10. A method for controlling undesirable vegetation, which comprises allowing a herbicidally effective amount of at least one thiochromanoylpyrazolone derivative of the formula I or an agriculturally useful salt of I as claimed in claim 1 to act on plants, their habitat and/or on seeds.

\* \* \* \* \*